(12) United States Patent
Tunc et al.

(10) Patent No.: US 10,080,661 B2
(45) Date of Patent: *Sep. 25, 2018

(54) INJECTABLE AND MOLDABLE BONE SUBSTITUTE MATERIALS

(71) Applicant: Warsaw Orthopedic, Inc., Warsaw, IN (US)

(72) Inventors: Deger C. Tunc, East Brunswick, NJ (US); John Winterbottom, Dundee, MI (US); David R. Kaes, Toms River, NJ (US); Todd Boyce, Collierville, TN (US); David Knaack, Summit, NJ (US); James Russell, Sarasota, FL (US); Subhabrata Bhattacharyya, Metuchen, NJ (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 60 days.

This patent is subject to a terminal disclaimer.

(21) Appl. No.: 15/149,920

(22) Filed: May 9, 2016

(65) Prior Publication Data

US 2016/0250025 A1 Sep. 1, 2016

Related U.S. Application Data

(63) Continuation of application No. 13/972,640, filed on Aug. 21, 2013, now Pat. No. 9,333,080, which is a continuation of application No. 11/625,119, filed on Jan. 19, 2007, now Pat. No. 9,107,751, and a continuation-in-part of application No. 11/047,992, filed on Jan. 31, 2005, now abandoned, and a continuation-in-part of application No. 10/735,135, filed on Dec. 12, 2003, now Pat. No. 7,291,345.

(60) Provisional application No. 60/760,538, filed on Jan. 19, 2006, provisional application No. 60/760,752, filed on Jan. 19, 2006, provisional application No. 60/760,753, filed on Jan. 19, 2006, provisional application No. 60/760,239, filed on Jan. 19, 2006, provisional application No. 60/568,472, filed on May 4, 2004, provisional application No. 60/432,968, filed on Dec. 12, 2002.

(51) Int. Cl.
| | |
|---|---|
| *A61K 9/00* | (2006.01) |
| *A61F 2/28* | (2006.01) |
| *A61L 27/44* | (2006.01) |
| *A61L 27/46* | (2006.01) |
| *A61L 27/48* | (2006.01) |
| *A61L 27/56* | (2006.01) |
| *A61L 27/58* | (2006.01) |
| *A61F 2/30* | (2006.01) |

(52) U.S. Cl.
CPC .............. *A61F 2/28* (2013.01); *A61L 27/446* (2013.01); *A61L 27/46* (2013.01); *A61L 27/48* (2013.01); *A61L 27/56* (2013.01); *A61L 27/58* (2013.01); *A61F 2002/2835* (2013.01); *A61F 2002/30062* (2013.01); *A61F 2002/30677* (2013.01); *A61F 2210/0004* (2013.01); *A61F 2310/00293* (2013.01); *A61F 2310/00359* (2013.01); *A61F 2310/00365* (2013.01); *A61L 2400/06* (2013.01); *A61L 2400/08* (2013.01); *A61L 2430/02* (2013.01)

(58) Field of Classification Search
CPC ... A61K 9/0012; A61K 9/0019; A61K 9/0024
See application file for complete search history.

(56) References Cited

U.S. PATENT DOCUMENTS

| | | | |
|---|---|---|---|
| 3,892,649 A | 7/1975 | Phillips et al. | 204/81 |
| 3,919,773 A | 11/1975 | Freeman | 32/10 A |
| 3,949,073 A | 4/1976 | Daniels et al. | 424/177 |
| 4,183,874 A | 1/1980 | Fan et al. | 525/100 |
| 4,551,156 A | 11/1985 | Li | 55/16 |
| 4,595,713 A | 6/1986 | St. John | |
| 4,637,931 A | 1/1987 | Schmitz | |
| 4,638,045 A | 1/1987 | Kohn et al. | |
| 4,645,503 A | 2/1987 | Lin et al. | 623/16 |
| 4,655,777 A | 4/1987 | Dunn et al. | 623/16 |
| 4,743,259 A | 5/1988 | Bolander et al. | |
| 4,783,504 A | 11/1988 | St. Clair et al. | 525/72 |
| 4,806,621 A | 2/1989 | Kohn et al. | |
| 4,880,610 A | 11/1989 | Constantz | |
| 4,882,149 A | 11/1989 | Spector | |
| RE33,161 E | 2/1990 | Brown et al. | |
| 4,902,296 A | 2/1990 | Bolander et al. | |
| 4,902,508 A | 2/1990 | Badylak | |
| RE33,221 E | 5/1990 | Brown et al. | |
| 4,946,929 A | 8/1990 | d'Amore et al. | |
| 5,010,167 A | 4/1991 | Ron et al. | |

(Continued)

FOREIGN PATENT DOCUMENTS

| | | |
|---|---|---|
| EP | 0 413 492 | 2/1991 |
| EP | 1044693 | 10/2000 |

(Continued)

OTHER PUBLICATIONS

Schmitz, et al., "A Preliminary Study of the Osteogenic Potential of a Biodegradable Alloplastic-Osteoinductive Alloimplant", *Clinical Orthopaedics and Related Research*, 237:245-255 (1988).

(Continued)

*Primary Examiner* — Ruth A Davis

(57) ABSTRACT

An osteoimplant composite comprising a plurality of particles of an inorganic material, a bone substitute material, a bone-derived material, or any combination thereof; and a polymer material with which the particles are combined. The composite is either naturally moldable or flowable, or it can be made moldable or settable. After implantation, the composite may be set to provide mechanical strength to the implant. The inventive composite have the advantage of being able to fill irregularly shape implantation site while at the same time being settable to provide the mechanical strength required for most orthopedic applications. The invention also provides methods of using and preparing the moldable and flowable composites.

19 Claims, No Drawings

(56) References Cited

U.S. PATENT DOCUMENTS

| | | |
|---|---|---|
| 5,019,379 A | 5/1991 | Domb et al. |
| 5,034,059 A | 7/1991 | Constantz |
| 5,047,031 A | 9/1991 | Constantz |
| 5,053,212 A | 10/1991 | Constantz |
| 5,073,373 A | 12/1991 | O'Leary |
| 5,129,905 A | 7/1992 | Constantz |
| 5,149,368 A | 9/1992 | Liu |
| 5,162,445 A | 11/1992 | Powers et al. ............. 525/333.4 |
| 5,236,456 A | 8/1993 | O'Leary |
| 5,246,782 A | 9/1993 | Kennedy et al. ............. 428/421 |
| 5,262,166 A | 11/1993 | Liu |
| 5,262,461 A | 11/1993 | Serizawa et al. ............. 524/262 |
| 5,263,984 A | 11/1993 | Li |
| 5,290,555 A | 3/1994 | Gurthauser et al. |
| 5,290,558 A | 3/1994 | O'Leary et al. |
| 5,324,519 A | 6/1994 | Dunn et al. ................... 424/426 |
| 5,333,626 A | 8/1994 | Morse et al. ................. 128/898 |
| 5,336,264 A | 8/1994 | Constantz |
| 5,352,715 A | 10/1994 | Wallace et al. |
| 5,399,665 A | 3/1995 | Barrera et al. |
| 5,417,975 A | 5/1995 | Lussi et al. |
| 5,462,722 A | 10/1995 | Liu |
| 5,468,544 A | 11/1995 | Marcolongo et al. ........ 428/224 |
| 5,507,810 A | 4/1996 | Prewett |
| 5,507,813 A | 4/1996 | Dowd et al. |
| 5,512,600 A | 4/1996 | Mikos et al. |
| 5,513,662 A | 5/1996 | Morse et al. ................. 128/898 |
| 5,514,378 A | 5/1996 | Mikos et al. |
| 5,525,148 A | 6/1996 | Chow |
| 5,542,973 A | 8/1996 | Chow |
| 5,552,454 A | 9/1996 | Kretschmann et al. |
| 5,573,771 A | 11/1996 | Geistlich et al. |
| 5,587,507 A | 12/1996 | Kohn |
| 5,605,713 A | 2/1997 | Boltong |
| 5,606,000 A | 2/1997 | Jadhav et al. .................. 528/29 |
| 5,607,269 A | 3/1997 | Dowd |
| 5,624,463 A | 4/1997 | Stone et al. |
| 5,626,861 A | 5/1997 | Laurencin et al. ........... 424/426 |
| 5,641,502 A | 6/1997 | Skalla et al. |
| 5,650,176 A | 7/1997 | Lee |
| 5,670,602 A | 9/1997 | Kohn |
| 5,679,723 A | 10/1997 | Cooper et al. |
| 5,696,175 A | 12/1997 | Mikos et al. |
| 5,716,404 A | 2/1998 | Vacanti et al. |
| 5,716,413 A | 2/1998 | Walter et al. |
| 5,717,006 A | 2/1998 | Daculsi |
| 5,736,372 A | 4/1998 | Vacanti et al. ................ 435/180 |
| 5,766,618 A | 6/1998 | Laurencin et al. ........... 424/426 |
| 5,766,637 A | 6/1998 | Shine et al. |
| 5,770,417 A | 6/1998 | Vacanti et al. |
| 5,804,178 A | 9/1998 | Vacanti et al. |
| 5,817,328 A | 10/1998 | Gresser et al. |
| 5,837,752 A | 11/1998 | Shastri et al. |
| 5,846,484 A | 12/1998 | Scarborough et al. ......... 422/28 |
| 5,846,951 A | 12/1998 | Gregoriadis |
| 5,863,297 A | 1/1999 | Walter et al. |
| 5,899,939 A | 5/1999 | Boyce et al. |
| 5,902,599 A | 5/1999 | Anseth et al. |
| 5,948,386 A | 9/1999 | Katti et al. ................... 424/1.77 |
| 5,977,204 A | 11/1999 | Boyan et al. |
| 6,001,394 A | 12/1999 | Daculsi |
| 6,002,065 A | 12/1999 | Constantz |
| 6,027,744 A | 2/2000 | Vacanti et al. ............... 424/426 |
| 6,030,635 A | 2/2000 | Gertzman et al. |
| 6,033,852 A | 3/2000 | Andle et al. |
| 6,077,989 A | 6/2000 | Kandel |
| 6,095,148 A | 8/2000 | Shastri et al. |
| 6,117,456 A | 9/2000 | Lee et al. |
| 6,119,028 A | 9/2000 | Schulman et al. |
| 6,120,491 A | 9/2000 | Kohn |
| 6,123,727 A | 9/2000 | Vacanti et al. |
| 6,123,731 A | 9/2000 | Boyce et al. |
| 6,127,442 A | 10/2000 | Sulzbach et al. |
| 6,132,468 A | 10/2000 | Mansmann ................ 623/20.16 |
| 6,156,068 A | 12/2000 | Walter et al. |
| 6,165,486 A | 12/2000 | Marra et al. ................... 424/423 |
| 6,180,606 B1 | 1/2001 | Chen et al. |
| 6,183,498 B1 | 2/2001 | Devore et al. |
| 6,203,573 B1 | 3/2001 | Walter et al. |
| 6,206,957 B1 | 3/2001 | Driessens |
| 6,224,630 B1 | 5/2001 | Bao et al. |
| 6,294,041 B1 | 9/2001 | Boyce et al. |
| 6,294,187 B1 | 9/2001 | Boyce et al. |
| 6,328,990 B1 | 12/2001 | Ducheyne et al. |
| 6,332,779 B1 | 12/2001 | Boyce et al. |
| 6,340,477 B1 | 1/2002 | Anderson |
| 6,352,667 B1 | 3/2002 | English .................... 264/328.17 |
| 6,376,573 B1 | 4/2002 | White et al. ................... 523/115 |
| 6,399,693 B1 | 6/2002 | Brennan et al. ............... 524/494 |
| 6,406,498 B1 | 6/2002 | Törmäläet al. ............. 623/23.75 |
| 6,432,436 B1 | 8/2002 | Gertzman et al. ............ 424/423 |
| 6,437,018 B1 | 8/2002 | Gertzman et al. |
| 6,440,444 B2 | 8/2002 | Boyce |
| 6,441,073 B1 | 8/2002 | Tanaka et al. |
| 6,471,993 B1 | 10/2002 | Shastri et al. ................ 424/486 |
| 6,478,825 B1 | 11/2002 | Winterbottom et al. |
| 6,511,511 B1 | 1/2003 | Slivka et al. ............... 623/23.75 |
| 6,599,516 B1 | 7/2003 | Knaack |
| 6,696,073 B2 | 2/2004 | Boyce et al. |
| RE38,522 E | 5/2004 | Gertzman et al. |
| 6,783,712 B2 | 8/2004 | Slivka et al. |
| 6,867,240 B2 | 3/2005 | Ma et al. |
| 6,911,212 B2 | 6/2005 | Gertzman et al. |
| 6,933,328 B2 | 8/2005 | Schact |
| 7,004,974 B1 | 2/2006 | Larsson et al. |
| 7,179,299 B2 | 2/2007 | Edwards |
| 7,270,813 B2 | 9/2007 | Shimp |
| 7,291,345 B2 | 11/2007 | Winterbottom |
| 9,107,751 B2* | 8/2015 | Winterbottom ........... A61F 2/28 |
| 9,333,080 B2* | 5/2016 | Tunc ........................ A61F 2/28 |
| 2001/0014831 A1 | 8/2001 | Scarborough |
| 2001/0051833 A1 | 12/2001 | Walter et al. |
| 2002/0035401 A1 | 3/2002 | Boyce et al. |
| 2002/0042378 A1 | 4/2002 | Reich |
| 2002/0098222 A1 | 7/2002 | Wironen et al. .............. 424/423 |
| 2003/0036800 A1 | 2/2003 | Meredith |
| 2003/0039676 A1 | 2/2003 | Boyce et al. |
| 2003/0045942 A1 | 3/2003 | Lai et al. |
| 2003/0065400 A1 | 4/2003 | Beam et al. |
| 2003/0114552 A1 | 6/2003 | Schacht |
| 2003/0114936 A1 | 6/2003 | Sherwood et al. |
| 2003/0144743 A1 | 7/2003 | Edwards et al. |
| 2003/0180344 A1 | 9/2003 | Wise et al. |
| 2003/0180364 A1 | 9/2003 | Chen |
| 2003/0206937 A1 | 11/2003 | Gertzman et al. |
| 2003/0235564 A1 | 12/2003 | Doll |
| 2003/0236573 A1 | 12/2003 | Evans et al. |
| 2004/0006153 A1 | 1/2004 | Seppala et al. |
| 2004/0024457 A1 | 2/2004 | Boyce et al. |
| 2004/0034434 A1 | 2/2004 | Evans et al. |
| 2004/0064193 A1 | 4/2004 | Evans et al. |
| 2004/0127987 A1 | 7/2004 | Evans et al. |
| 2004/0137032 A1 | 7/2004 | Wang |
| 2004/0138758 A1 | 7/2004 | Evans et al. |
| 2004/0146543 A1 | 7/2004 | Shimp et al. |
| 2004/0197373 A1 | 10/2004 | Gertzman et al. |
| 2004/0228898 A1 | 11/2004 | Ross et al. |
| 2004/0253290 A1 | 12/2004 | Kim et al. |
| 2005/0008620 A1 | 1/2005 | Shimp et al. |
| 2005/0008672 A1 | 1/2005 | Winterbottom |
| 2005/0013793 A1 | 1/2005 | Beckamn et al. |
| 2005/0027033 A1 | 2/2005 | Knaack et al. |
| 2005/0031704 A1 | 2/2005 | Ahn |
| 2005/0042253 A1 | 2/2005 | Farrar |
| 2005/0100578 A1 | 5/2005 | Schmid et al. |
| 2005/0129726 A1 | 6/2005 | Liebschner |
| 2005/0238683 A1 | 10/2005 | Adhikari et al. |
| 2005/0249773 A1 | 11/2005 | Maspero et al. |
| 2005/0251266 A1 | 11/2005 | Maspero et al. |
| 2005/0251267 A1 | 11/2005 | Winterbottom |
| 2005/0281856 A1 | 12/2005 | McGlohorn et al. |
| 2006/0015184 A1 | 1/2006 | Winterbottom |
| 2006/0067971 A1 | 3/2006 | Story et al. |
| 2006/0067973 A1 | 3/2006 | Schachter |

(56) References Cited

U.S. PATENT DOCUMENTS

| | | |
|---|---|---|
| 2006/0127442 A1 | 6/2006 | Helmus |
| 2006/0204581 A1 | 9/2006 | Gower et al. |
| 2006/0216323 A1 | 9/2006 | Knaack et al. |
| 2006/0263335 A1 | 11/2006 | France et al. |
| 2008/0009955 A1 | 1/2008 | Shimp |
| 2008/0063684 A1 | 3/2008 | Winterbottom |

FOREIGN PATENT DOCUMENTS

| | | |
|---|---|---|
| JP | 01-501208 | 4/1989 |
| JP | 11-192299 | 7/1999 |
| JP | 11-513590 | 11/1999 |
| JP | 2001-518321 | 10/2001 |
| JP | 2002-537073 | 11/2002 |
| WO | WO 88/01517 | 3/1988 |
| WO | WO-91/09079 | 6/1991 |
| WO | WO 97/14376 | 4/1997 |
| WO | WO 98/19718 | 5/1998 |
| WO | WO-98/19718 | 5/1998 |
| WO | WO 99/16478 | 4/1999 |
| WO | WO 00/50102 | 8/2000 |
| WO | WO-02/056929 | 7/2002 |
| WO | WO 02/068009 | 9/2002 |
| WO | WO-02/083188 | 10/2002 |
| WO | WO-02/083194 | 10/2002 |
| WO | WO 03/030956 | 4/2003 |
| WO | WO 03/065996 | 8/2003 |
| WO | WO-04/053112 | 12/2003 |
| WO | WO 04/014452 | 2/2004 |
| WO | WO 04/017857 | 3/2004 |
| WO | WO-2004/032988 | 4/2004 |
| WO | WO 05/65396 | 7/2005 |

OTHER PUBLICATIONS

U.S. Appl. No. 10/639,912, filed Aug. 12, 2003, Shimp et al.
U.S. Appl. No. 10/681,651, filed Oct. 8, 2003, Shimp et al.
International Search Report for PCT/US03/25417.
International Search Report for PCT/US03/39704.
Baker, Gregory L., http://www.cem.msu.edu/~gradoff/brochf/Baker.htm, printed Aug. 2002.
Boesch, P., "Bone Grafting with Fibrin Glue", *Wiener Klinische Wochenschroft Supplementum*, 93, No. 124, pp. 3-26, 1981.
Han, et al., "Synergistic Effects of Lecithin and Human DBM on Bone Induction in Nude Rats", *Society for Biomaterials*, 28th Annual Meeting Transactions, 2002 (abstract).
Hooper, et al., "Diphenolic Monomers Derived from the Natural Amino Acid α-L-Tyrosine: An Evaluation of Peptide Coupling Techniques", *Journal of Bioactive and Compatible Polymers* 10, 327-340 (1995).
Nazhat, S.N., et al., "Dynamic Mechanical Behaviour of Modified Hydroxyapatite Reinforced Polyethylene Composites", *Fifth World Biomaterials Congress*, p. 83, May 29-Jun. 2, 1996.
Satish Pulapura, et al., "Tyrosine-Derived Polycarbonates: Backbone-Modified "Pseudo"-Poly (Amino Acids) Designed for Biomedical Applications", *Biopolymers* 32, 411-417 (1992).
"Silane Coupling Agent", http://www.apr.co.kr/silaneen.htm, printed Aug. 7, 2002.
Simmons, D.M., et al., "Evaluation of collagen cross-linking techniques for the stabilization of tissue matrices", *Biotechnol. Appl. Biochem.* 17, 23-29 (1993) (abstract only).
Tangpasuthadol, Varawut, "Thermo-Mechanical Properties and Hydrolytic Degradation of Tyrosine-Derived Polymers for Use in Biomedical Applications", Ph.D. Dissertation, Rutgers, The State University of New Jersey, (Jan. 1999).
Whittaker, et al., "Matrix Metalloproteinases and their Inhibitors—Current Status and Future Challenges", *Celltransmissions*, 17, prior to Jun. 13, 2002.
Zhiyuan Zhong, et al., "Calcium methoxide initiated ring-opening polymerization of ε-caprolactone and L-lactide", *Polymer Bulletin* 46, 51-57 (2001).
Garboczi, et al., Geometrical Percolation Threshold of Overlapping Ellipsoids, Phys. Rev. E, 1995, 52(1):819.
Lewandrowski, et al., J. Biomed. Mater. Res., 1996, 31:365-372.
Noorjahan et al., J. Biomed. Materials Research, Part B, Applied Biomaterials (2005), vol. 75(20): 343-350.
Reddi, et al., Proc. Nat. Acad. Sci., 1972, 69:1601-1605.
Ohgushi et al., Bioceramics (1997), vol. 10: 233-236.
Simmons, et al., "Evaluation of collagen cross-linking techniques for the stabilization of tissue matrices" Biotechnol. Appl. Biochem, 1993, 17:23:29.
Stevenson, et al., "Factors affecting bone graft incorporation" Clin. Orthop. Rel. Res., 1996, 324:66-74.
Tangpasuthadol, et al., Hydrolytic degradation of tyrosine derived polycarbonates, a class of new biomaterials. Part II:3: 3-yr study of polymeric devices. Biomaterials, 2000 21:2379 87.
Tangpasuthadol, et al., Hydrolytic degradation of tyrosine derived polycarbonates, a class of new biomaterials. Part I: study of model compounds. Biomaterials, 2000 21:2371 8.
Urist MR, A morphogenetic matrix for differentiation of bone tissue, Calcif Tissue Res. 1970; Suppl:98-101.
Urist MR, Bone: formation by autoinduction, Science, Nov. 12, 1965; 150(698):893-9.
Chu, TM et al., "Hydroxyapatite implants with designed internal architecture" J. Material Science: Materials in medicine 2001, vol. 12: 471-478.
Hockin, HK et al., "Synergistic reinforcement of in situ hardening calcium phosphate composite scaffold for bone tissue engineering" Biomaterials, 2003, vol. 25(6): 1029-1037.
Arinzeh, TL et al., "Allogenic Mesenchymal Stem Cells Regenerate Bone in Critical-Sized Canine Segmental Defect", J. of Bone and Joint Surgery, American vol. 85-A(10), Oct. 2003: 1927-35.
Ushio et al., "Attachment of Artificial Cartilage to Underlying Bone", Wiley InerScience 2003.
Boyce TM, "Cellular Penetration and Bone Formation Depends upon Allograft Bone Fraction in a Loadbearing Composite Implant", Trans Soc. Biomaterials 2005:p. 133.
Simon et al., Engineered cellular response to scaffold architecture in a rabbit trephine defect, J Biomed Mater Res A, 2003, vol. 66, No. 2, pp. 275-282.
Schmitz, et al., "A Preliminary Study of the Osteogenic Potential of a Biodegradable Alloplastic-Osteoinductive Alloimplant", Clinical Orthopedics and Related Research, 237:245-255 (1988).
International Search Report of PCT Application No. PCT/US05/15426.
Reddi et al., "Biochemical Sequences in the Transformation of Normal Fibroblasts in Adolescent Rats", *Proc. Natl. Acad. Sci. USA*, 69:1601-5, 1972.
Lewandrowski et al., "Kinetics of cortical bone demineralization: Controlled demineralization—a new method for modifying cortical bone allografts", *J. Biomed. Mater. Res.*, 31: 365-72, 1996.
Hurley et al., "Anorganic Bone—Chemistry, Anatomy, and Biological Reactions" *Milit. Med.*, 101-4, 1957.
Kershaw, "Preparation of Anorganic Bone Grafting Material", *Pharm. J.*, 6: 537, 1963.
De Wijn et al., "Grafting PMMA on Hydroxyapatite Powder Particles using Isocyanatoethylmethacrylate", Fifth World Biomaterials Congress, May 29-Jun. 2, 1996, Toronto, CA.
Simmons et al., "Evaluation of collagen cross-linking techniques for the stabilization of tissue matrices", *Biotechnol. Appl. Biochem.*, 17: 23-9, 1993.
James et al., "Small changes in polymer chemistry have a large effect on the bone-implant interface: evaluation of a series of degradable tyrosine-derived polycarbonates in bone defects", *Biomaterials*, 20: 2203-313, 1999.
Langer, "Biomaterials in drug delivery and tissue engineering: one laboratory's experience", Acc. *Chem. Res.*, 33: 94, 2000.
Langer, "Selected advances in drug delivery and tissue engineering", *J. Control Release*, 62: 7, 1999.
Uhrich et al., "Polymeric systems for controlled drug release", *Chem. Rev.*, 99: 3181, 1999.
Allcock et al., "Synthesis of poly (amino acid alkyl ester) phosphazenes", *Macromolecules*, 10: 824-30, 1977.

(56) References Cited

OTHER PUBLICATIONS

Allcock et al., "Hydrolysis pathways for aminophosphazenes", *Inorg. Chem.*, 21: 515-21, 1982.

Mikos et al., "Prevascularization of biodegradable polymer scaffolds for hepatocyte transplantation", *Proc. ACS Div. of Polymer Mater.*, 66: 33, 1992.

Eggli et al., "Porous Hydroxyapatite and tricalcium phosphate cylinders with two different pore size ranges implanted in the cancellous bone of rabbits", *Clin Orthop.*, 232: 127-38, 1987.

White et al., "Biomaterial aspects of Interpore 200 porous hydroxyapatite", *Dental Cliical of N. Amer.*, 30: 49-67, 1986.

Klaitwatter et al., "Application of porous ceramics for the attachment of load bering orthopedic applications", *J. Biomed. Mater. Res. Symp.*, 2: 161, 1971.

Murphy et al., "Salt Fusion: An Approach to Improve Pore Interconeectivity withing Tissue Engineering Scaffolds", *Tissue Engineering*, 8(1): 43-52, 2002.

Karageorgiou et al., "Porosity of 3D biomaterial scaffolds and osteogenesis", *Biomaterials*, 26: 5474-91, 2005.

Bohner et al., "Theoretical and experimental model to describe the injection of a polymethylmethacrylate cement into a porous structure", *Biomaterials*, 24: 2721-30, 2003.

Bohner et al., "Injectability of calcium phosphate pastes", *Biomaterials*, 26: 1553-63, 2005.

Giannitsios et al.,"High Cement Viscosity Reduces Leakage Risk in Vertebroplasty", European Cells and Materials, 10(3): 54, 2005.

Vogt et al., "Fabrication of Highly Porous Scaffold Materials based on Functionalized Oligolactides and Preliminary Results on Their Use in Bone Tissue Engineering", *European Cells and Materials*, 4: 30-38, 2002.

Schmitz et al., "A Preliminary Study of the Osteogenic Potential of a Biodegradable Alloplastic-Osteoinductive Alloimplant", *Clinical Orthopaedics and Related Research*, 237: 245-55, 1988.

International Search Report, PCT/US05/15426, dated Jun. 15, 2006.

International Search Report for PCT/US03/25417, dated Jul. 2, 2004.

International Search Report for PCT/US03/39704, dated Jun. 2, 2004.

Forssell et al., "Experimental Osteosynthesis with Liquid Ethyl Cyanacrylate Polymerized with Ultrasound", *Arch. Orthop Trauma Surg*, 103: 278-83, 1984.

Liu et al., "Covalent Bonding of PMMA, PBMA, and ply(HEMA) to Hydroxyapatite Particles", *J. Biomed. Mater. Res.*, 40: 257-63, 1998.

Tangpasuthadol, et al., Hydrolytic degradation of tyrosine derived polycarbonates, a class of new biomaterials. Part II:3: 3-yr study of polymeric devices. Biomaterials, 2000 21:2379 87.

International Searching Authority, "International Search Report," PCT Application No. PCT/US05/15426, 4 pgs.

International Searching Authority, "Written Opinion," PCT Application No. PCT/US05/15426, 5 pgs.

\* cited by examiner

INJECTABLE AND MOLDABLE BONE SUBSTITUTE MATERIALS

RELATED APPLICATIONS

The present application claims priority under 35 U.S.C. § 120 and is a continuation of U.S. patent application Ser. No. 13/972,640, filed Aug. 21, 2013, which claims priority to U.S. patent application Ser. No. 11/625,119, filed Jan. 19, 2007, now issued as U.S. Pat. No. 9,107,751, and is a continuation-in-part of U.S. patent application Ser. No. 10/735,135, filed Dec. 12, 2003, now issued as U.S. Pat. No. 7,291,345, which claims priority under 35 U.S.C. § 119(e) to provisional patent application Ser. No. 60/432,968, filed Dec. 12, 2002; each of which is incorporated herein by reference in their entirety. The present application also claims priority under 35 U.S.C. § 120 and is a continuation-in-part of U.S. patent application Ser. No. 11/047,992, filed Jan. 31, 2005, which claims priority under 35 U.S.C. § 119(e) to provisional patent application Ser. No. 60/568,472, filed May 4, 2004; each of which is incorporated herein by reference in their entirety. The present application also claims priority under 35 U.S.C. § 119(e) to U.S. provisional patent application Ser. No. 60/760,538, Ser. No. 60/760,752, Ser. No. 60/760,753, and Ser. No. 60/760,239, all of which were filed Jan. 19, 2006, each of which is incorporated herein by reference in their entirety.

FIELD OF THE INVENTION

This invention pertains to injectable and moldable polymer-bone composites that set upon exposure to certain predetermined conditions for use in orthopedic medicine.

BACKGROUND OF THE INVENTION

Bone is a composite material composed of impure hydroxyapatite, collagen, and a variety of non-collagenous proteins, as well as embedded and adherent cells. Bone can be processed into an implantable biomaterial, such as an allograft, for example, by removing the cells, leaving behind the extracellular matrix. The processed bone biomaterial can have a variety of properties, depending upon the specific processes and treatments applied to it, and may incorporate characteristics of other biomaterials with which it is combined. For example, bone-derived biomaterials may be processed into load-bearing mineralized grafts that support and integrate with the patient's own bone or may alternatively be processed into soft, moldable, or flowable demineralized bone biomaterials that have the ability to induce a cellular healing response.

The use of bone grafts and bone substitute materials in orthopedic medicine is well known. While bone wounds can regenerate without the formation of scar tissue, fractures and other orthopedic injuries take a long time to heal, during which the injured bone is unable to support physiologic loading. Metal pins, screws, and meshes are frequently needed to replace the mechanical functions of injured bone. However, metal is significantly stiffer than bone. Use of metal implants may result in decreased bone density around the implant site due to stress shielding. Furthermore, most metal implants are permanent and unable to participate in physiological remodeling.

Bone's cellular healing processes, through bone tissue formation by osteoblast cells coordinated with bone and graft resorption by osteoclast cells, permit bone grafts and certain bone substitute materials to remodel into endogenous bone that is almost indistinguishable from the original. However, the use of bone grafts is limited by the available shape and size of grafts and the desire to optimize both mechanical strength and degradation rate. Variations in bone size and shape among patients (and donors) also make bone grafts a less optimal substitute material. Bone substitute materials and bone chips are quickly remodeled but cannot immediately provide mechanical support. In contrast, cortical bone grafts can support physiological stresses but remodel slowly.

U.S. Pat. Nos. 5,899,939; 5,507,813; 6,123,731; 6,294,041; 6,294,187; 6,332,779; 6,440,444; and 6,478,825; the contents of all of which are incorporated herein by reference, describe methods for preparing composites including allogenic bone for use in load bearing orthopedic applications.

Thus, it is desirable to have a bone substitute material for structural grafts that may be produced in larger quantities than grafts derived solely from bone and that may be fabricated or molded into shapes without being limited by the shape of the originating tissue. It is also desirable to have injectable bone substitute materials that may be implanted using minimally invasive techniques.

SUMMARY OF THE INVENTION

The present invention stems from the recognition that bone substitute material is needed that is moldable or injectable to fill irregularly shaped volumes in or near a bone. A bone substitute material that is moldable and/or flowable while being implanted but later becoming set with a desired degree of mechanical strength would be particularly useful in treating bony defects in a subject. The bone substitute material could be molded, shaped, or injected into the site of implantation and then set under predetermined suitable conditions such as cooling to body temperature. The set material would provide the desired mechanical strength for the implantation site reducing the need for metal pins, screws, or meshes. The present invention provides such bone substitute composite materials made up of particles of inorganic material, a bone substitute material, and/or a bone-derived material, and a polymer, wherein the composite is moldable or flowable, and it can be set upon exposure to suitable conditions. Processes for preparing and using these materials, and kits for easy administration of the inventive materials are also provided.

In one aspect, the invention provides compositions including a plurality of particles of an inorganic material, a bone substitute material, a bone-derived material, or any combination thereof, and a polymer with which the particles are combined. The composite of the particles and the polymer is naturally moldable or flowable, or the composite can be made moldable or flowable such as by heating or by the addition of a solvent. The composition may range from a thick, flowable liquid to a moldable, dough-like substance. In certain embodiments, the composite has a low enough viscosity to be suitable for injection. In other embodiments, the composite is workable so that it can be molded into an implantation site. The composite becomes set upon exposure to certain predetermined suitable conditions. The conditions for setting will of course depend on the composite being used. Exemplary conditions for setting the composite may include a change in temperature (e.g., heating or cooling), a change in osmotic pressure, exposure to electromagnetic radiation (e.g., microwaves, IR radiation, visible light, UV radiation), cross-linking the composite, exposing the composite to a chemical agent, a change in the content of water or other solvent in the composite, a change in the content of a component of the composite, or a change in a diffusion gradient. The particles in the composite have an average size of about 10 to about 1000 microns in diameter, preferably an average size of about 20 to about 800 microns in diameter. In certain embodiments, the median size of the particles ranges from about 10 to about 1000 microns in diameter, preferably from about 20 to about 800 microns. Smaller or large particles may also be found in the composite. A particle size distribution of the particles with respect to a median value may be plus and minus about 90% or less, about 50% or less, or about 20% or less. In certain embodiments, at least about 60% of the particles have a median size of about 10 microns to about 1000 microns in their greatest dimension. In certain embodiments, at least about 60% of the particles have a median size of about 20 microns to about 800 microns in their greatest dimension.

The polymer used in preparing the inventive composite may be selected from monomers, pre-polymers, oligomers, polymers, cross-linked polymers, partially polymerized polymers, partially cross-linked polymers, and any combinations thereof. For example, the composite may include monomers, oligomers, and polymers. Exemplary polymers useful in the inventive composites include, but are not limited to, poly(lactide), poly(glycolide), poly(lactide-co-glycolide), poly(D,L-lactide-co-glycolide), poly(L-lactide-co-glycolide), poly(caprolactone), polyurethane, polycarbonates, polyarylates, polypropylene fumarates), polyphosphazines, and combinations, blends, or co-polymers thereof.

In certain embodiments, the composite include particles of bone-derived material. The bone-derived material of such composites may include one or more of nondemineralized bone particles, demineralized bone particles, lightly demineralized bone particles, and deorganified bone particles. The bone-derived material may include one or more of cortical bone, cancellous bone, and cortico-cancellous bone. Also, the bone-derived material may include autogenous bone, allogenic bone, and xenogeneic bone. In certain embodiments, the composite includes an inorganic material (e.g., an inorganic ceramic) and/or a bone substitute material. Exemplary inorganic materials or bone substitute materials useful in the inventive composites include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, BIOGLASS™, fluorapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium, sodium, potassium, etc.), and combinations and derivatives thereof. In certain embodiments, the particles themselves are composites that include one or more of an inorganic material, a bone substitute material, and a bone-derived material; and one or more of bovine serum albumin, collagen, an extracellular matrix component, a synthetic polymer, and a natural polymer. The composite may range from approximately 10% particles to about 95% particles by weight, for example, approximately 50% particles to approximately 80% particles by weight. In certain embodiments, the composite is approximately 50%, approximately 55%, approximately 60%, or approximately 65% particles by weight. The composite may also include other components. For example, the composite may further include one or more of an initiator, accelerator, catalyst, solvent, wetting agent, lubricating agent, labeling agent, plasticizer, radiopacifier, porogen, bioactive agent, biostatic agent, cell, polynucleotide, protein (e.g., bone morphogenic protein, cytokine, growth factor, aniogenic factor), pharmaceutical agent (e.g., anti-inflammatory agent, analgesic, antibiotic, etc.), and pharmaceutically acceptable excipient. In certain embodiments, the composite includes a plasticizer that softens the composite making it more pliable. Exemplary plasticizer include glycerol and poly(ethylene glycol) (PEG) (e.g., PEG 8000, PEG 6000, PEG 4000). In certain embodiments, the polymer component of the composite includes PEG blended, grafted, or co-polymerized with the polymer. In certain embodiments, the composite includes a porogen that diffuses, dissolves, and/or degrades after implantation of the composite leaving a pore. The porogen may be a gas (e.g., carbon dioxide, nitrogen), liquid (e.g., water), or solid (e.g., crystalline salt). The porogen may be a water-soluble chemical compound such as a carbohydrate (e.g., poly(dextrose), dextran), salt, polymer (e.g., polyvinyl pyrrolidone), protein (e.g., gelatin), pharmaceutical agent (e.g., antibiotics), small molecule, etc.

In another aspect, the invention provides a method of administering an inventive composite to a subject in need thereof. The inventive composites are particularly useful in orthopedic medicine. The composite may be used to repair a fracture or other bony defect in a subject's bone. The method includes providing a flowable or moldable composite of a polymer and a plurality of particles including one or more of an inorganic material, a bone substitute material, and a bone-derived material; administering the composite to a subject in need thereof; and causing the composite to set. Before administration, the composite may be made flowable or moldable by heating the composite or adding a solvent to the composite. The composite is administered into an implantation site (e.g., a bony defect) followed by setting the composite. The composite may be set by allowing the composite to come to body temperature, increasing the molecular weight of the polymer in the composite, cross-linking the polymer in the composite, irradiating the composite with UV radiation, adding a chemical agent to the polymer, or allowing a solvent to diffuse from the composite. The set osteoimplant composite is allowed to remain at the site providing the strength desired while at the same time promoting healing of the bone and/or bone growth. The polymer component of the composite may degraded or be resorbed as new bone is formed at the implantation site. The polymer may be resorbed over approximately 1 month to approximately 6 years. The composite may start to be remodeled in as little as a week as the composite is infiltrated with cells or new bone in-growth. The remodeling process may continue for weeks, months, or years.

In yet another aspect, the invention provide a method of preparing the inventive composites by combining a plurality of particles comprising an inorganic material, a bone substitute material, a bone-derived material, or combinations thereof; and a polymer (e.g., polycaprolactone, poly(lactide), poly(glycolide), poly(lactide-co-glycodide), polyurethane); and heating the resulting composite until is becomes moldable (e.g., to a temperature between approximately 40° C. and approximately 80° C.). Once the composite is implanted and allowed to cool to body temperature (approximately 37° C.), the composite becomes set. The invention also provides another method of preparing the inventive composites by combining a plurality of particles comprising an inorganic material, a bone substitute material, a bone-derived material, or combinations thereof; and a polymer (e.g., polycaprolactone, poly(lactide), poly(glycolide), poly (lactide-co-glycodide), polyurethane); and adding a solvent or pharmaceutically acceptable excipient so that the resulting composite is flowable or moldable. The composite may then be injected or placed into the site of implantation. As the solvent or excipient diffuses out of the composite, it becomes set in place.

In another embodiment, the invention provides kits for the treatment of bone. The kit includes a composition including a plurality of particles including one or more of an inorganic material, a bone substitute material, and a bone-derived material; and a polymer with which the particles are combined, the composition being contained within a delivery system for delivering the composite by injection (e.g., a syringe). The kit may also include a high pressure injection device for implanting composite of higher viscosity. The injection device may operate by hydraulic or pneumatic means. The kit may also include the components of the composite packaged separately for mixing just prior to implantation. The composite is preferably sterilely packaged. In certain embodiments, the entire kit is sterilely packaged for use in a sterile environment such as an operating room. Various amounts of the composite may be packaged in a kit. For larger implantation sites, kits with greater amounts of composite are used. The amount of composite packaged in a kit may depend on the procedure being performed on the subject. In certain embodiments, multiple individually packaged amounts of composite are included in one kit. That way only the necessary number of packages need be opened for a procedure. The kit may also include a heating apparatus for warming the composite to a temperature where it is moldable. The kit may also include a solvent or pharmaceutically acceptable excipient for combining with the composite. The kit may further include instructions for using the composite.

Definitions

As used herein, "bioactive agent" is used to refer to compounds or entities that alter, promote, speed, prolong, inhibit, activate, or otherwise affect biological or chemical events in a subject (e.g., a human). For example, bioactive agents may include, but are not limited to osteogenic, osteoinductive, and osteoconductive agents, anti-HIV substances, anti-cancer substances, antibiotics, immunosuppressants, anti-viral agents, enzyme inhibitors, neurotoxins, opioids, hypnotics, anti-histamines, lubricants, tranquilizers, anti-convulsants, muscle relaxants, anti-Parkinson agents, anti-spasmodics and muscle contractants including channel blockers, miotics and anti-cholinergics, anti-glaucoma compounds, anti-parasite agents, anti-protozoal agents, and/or anti-fungal agents, modulators of cell-extracellular matrix interactions including cell growth inhibitors and anti-adhesion molecules, vasodilating agents, inhibitors of DNA, RNA, or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotics, targeting agents, chemotactic factors, receptors, neurotransmitters, proteins, cell response modifiers, cells, peptides, polynucleotides, viruses, and vaccines. In certain preferred embodiments, the bioactive agent is a drug. In certain embodiments, the bioactive agent is a small molecule.

A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al., CRC Press, 1996, the United States Pharmacopeia-25/National Formulary-20, published by the United States Pharmcopeial Convention, Inc., Rockville Md., 2001, and the "Pharmazeutische Wirkstoffe", edited by Von Keemann et al., Stuttgart/New York, 1987, all of which are incorporated herein by reference. Drugs for human use listed by the U.S. Food and Drug Administration (FDA) under 21 C.F.R. §§ 330.5, 331 through 361, and 440 through 460, and drugs for veterinary use listed by the FDA under 21 C.F.R. §§ 500 through 589, all of which are incorporated herein by reference, are also considered acceptable for use in accordance with the present invention.

As used herein, "biodegradable", "bioerodable", or "resorbable" materials are materials that degrade under physiological conditions to form a product that can be metabolized or excreted without damage to the subject. In certain embodiments, the product is metabolized or excreted without permanent damage to the subject. Biodegradable materials may be hydrolytically degradable, may require cellular and/or enzymatic action to fully degrade, or both. Other degradation mechanisms, e.g., thermal degradation due to body heat, are also envisioned. Biodegradable materials also include materials that are broken down within cells. Degradation may occur by hydrolysis, enzymatic processes, phagocytosis, or other processes.

The term "biocompatible", as used herein, is intended to describe materials that, upon administration in vivo, do not induce undesirable side effects. The material preferably does not induce irreversible, undesirable side effects. In certain embodiments, a material is biocompatible if it does not induce long term undesirable side effects. In certain embodiments, the risks and benefits of administering a material are weighed in order to determine whether a material is sufficiently biocompatible to be administered to a subject.

The term "biomolecules", as used herein, refers to classes of molecules (e.g., proteins, amino acids, peptides, polynucleotides, nucleotides, carbohydrates, sugars, lipids, nucleoproteins, glycoproteins, lipoproteins, steroids, natural products, etc.) that are commonly found or produced in cells, whether the molecules themselves are naturally-occurring or artificially created (e.g., by synthetic or recombinant methods). For example, biomolecules include, but are not limited to, enzymes, receptors, glycosaminoglycans, neurotransmitters, hormones, cytokines, cell response modifiers such as growth factors and chemotactic factors, antibodies, vaccines, haptens, toxins, interferons, ribozymes, anti-sense agents, plasmids, DNA, and RNA. Exemplary growth factors include but are not limited to bone morphogenic proteins (BMP's) and their active fragments or subunits. In some embodiments, the biomolecule is a growth factor, chemotactic factor, cytokine, extracellular matrix molecule, or a fragment or derivative thereof, for example, a cell attachment sequence such as a peptide containing the sequence, RGD.

The term "tissue-derived material", as used herein, refers to a material that is obtained from an animal tissue. A tissue-derived material may include the tissue itself, a portion thereof, or one or more components thereof. For example, bone-derived tissue includes a whole bone, a bone particle, and bone or bone pieces that have been processed to remove one or more of cells, collagen, other extracellular matrix components, mineral, etc. In certain embodiments, tissue-derived material is treated to removed any infectious agents, in particular, pathogens (e.g., viruses, bacteria, fungi, parasites, etc.) In certain embodiments, tissue-derived material is treated to kill or remove any living cells or viruses. In certain particular embodiments, the tissue-derived material includes the extracellular matrix portion of a tissue. In certain embodiments, the tissue-derived material is purified extracellular matrix.

The term "carbohydrate" refers to a sugar or polymer of sugars. The terms "saccharide", "polysaccharide", "carbohydrate", and "oligosaccharide", may be used interchangeably. Most carbohydrates are aldehydes or ketones with many hydroxyl groups, usually one on each carbon atom of the molecule. Carbohydrates generally have the molecular formula $C_nH_{2n}O_n$. A carbohydrate may be a monosaccharide, a disaccharide, trisaccharide, oligosaccharide, or polysaccharide. The most basic carbohydrate is a monosaccharide, such as glucose, sucrose, galactose, mannose, ribose, arabinose, xylose, and fructose. Disaccharides are two joined monosaccharides. Exemplary disaccharides include sucrose, maltose, cellobiose, and lactose. Typically, an oligosaccharide includes between three and six monosaccharide units (e.g., raffinose, stachyose), and polysaccharides include six or more monosaccharide units. Exemplary polysaccharides include starch, glycogen, and cellulose. Carbohydrates may contain modified saccharide units such as 2'-deoxyribose wherein a hydroxyl group is removed, 2'-fluororibose wherein a hydroxyl group is replace with a fluorine, or N-acetylglucosamine, a nitrogen-containing form of glucose. (e.g., 2'-fluororibose, deoxyribose, and hexose). Carbohydrates may exist in many different forms, for example, conformers, cyclic forms, acyclic forms, stereoisomers, tautomers, anomers, and isomers.

The term "composite" is used to refer to a unified combination of two or more distinct materials. The composite may be homogeneous or heterogeneous. For example, a composite may be a combination of bone-derived particles and a polymer; or a combination of a bone substitute material and a polymer. In certain embodiments, the composite has a particular orientation.

"Demineralized" is used to refer to bone-derived material (e.g., particles) that have been subjected to a process that causes a decrease in the original mineral content. As utilized herein, the phrase "superficially demineralized" as applied to bone particles refers to bone particles possessing at least about 90% by weight of their original inorganic mineral content. The phrase "partially demineralized" as applied to the bone particles refers to bone particles possessing from about 8% to about 90% by weight of their original inorganic mineral content, and the phrase "fully demineralized" as applied to the bone particles refers to bone particles possessing less than about 8% by weight, for example, less than about 1% by weight, of their original inorganic mineral content. The unmodified term "demineralized" as applied to the bone particles is intended to cover any one or combination of the foregoing types of demineralized bone particles.

"Deorganified", as herein applied to matrices, particles, etc., refers to bone or cartilage matrices, particles, etc., that were subjected to a process that removes at least part of their original organic content. In some embodiments, at least 1%, 10%, 20%, 30%, 40%, 50%, 60%, 70%, 80%, 90%, or 99% of the organic content of the starting material is removed. Deorganified bone from which substantially all the organic components have been removed is termed "anorganic."

The term "electromagnetic radiation" refers to a self-propagating wave with both electric and magnetic components. The wave travels at the speed of light through a vacuum. The magnetic and electric components oscillate at right angles to each other and also to the direction of propagation of the wave. Electromagnetic radiation is typically classified according to the frequency of the wave. In order of increasing frequency, they are radio waves, microwaves, infrared (IR) radiation, visible light, ultraviolet (UV) radiation, X-rays, and gamma rays. In certain contexts, electromagnetic radiation is referred to as light.

As used herein, the term "flowable polymer material" refers to a composition including one or more of monomers, pre-polymers, oligomers, low molecular weight polymers, uncross-linked polymers, partially cross-linked polymers, partially polymerized polymers, polymers, or combinations thereof that have been rendered formable. One skilled in the art will recognize that the flowable polymer material need not be a polymer but may be polymerizable. In some embodiments, flowable polymer materials include polymers that have been heated past their glass transition or melting point. Alternatively or in addition, a flowable polymer material may include partially polymerized polymer, telechelic polymer, or prepolymer. A pre-polymer is a low molecular weight oligomer typically produced through step growth polymerization. The pre-polymer is formed with an excess of one of the components to produce molecules that are all terminated with the same group. For example, a diol and an excess of a diisocyanate may be polymerized to produce isocyanate terminated prepolymer that may be combined with a diol to form a polyurethane. Alternatively or in addition, the flowable polymer material may be a polymer material/solvent mixture that sets when the solvent is removed.

As used herein, "formable" materials are those that can be shaped by mechanical deformation. Exemplary methods of deformation include, without limitation, injection molding, extrusion, injection, pressing, casting, rolling, and molding.

As used herein, the term "glass transition temperature" ($T_g$) indicates the lowest temperature at which an amorphous or partially amorphous polymer is considered softened and possibly flowable. As referred to herein, the value of $T_g$ is to be determined using differential calorimetry as per ASTM Standard E1356-98 "Standard Test Method for Assignment of the Glass Transition Temperatures by Differential Scanning Calorimetry or Differential Thermal Analysis."

As used herein, the term "melting temperature" ($T_m$) is defined as the temperature, at atmospheric pressure, at which a polymer transitions from a crystalline state to a viscous flow state. As referred to herein, the value of $T_m$ is the value of $T_{pm1}$ as determined according to per ASTM Standard D3418-99 "Standard Test Method for Transition Temperatures of Polymers By Differential Scanning Calorimetry."

The term "mineralized" refers to bone-derived materials that have been subjected to a process that caused a decrease in their original organic content (e.g., de-fatting, de-greasing). Such a process results in an increase in the relative inorganic mineral content of the bone-derived material. Mineralization may also refer to the mineralization of a matrix such as extracellular matrix or demineralized bone matrix. The mineralization process may take either in vivo or in vitro.

"Non-demineralized", as herein applied to bone or bone particles, refers to bone or bone-derived material (e.g., particles) that have not been subjected to a demineralization process (i.e., a procedure that totally or partially removes the original inorganic content of bone).

The term "osteoconductive", as used herein, refers to the ability of a substance or material to provide surfaces which are receptive to the growth of new bone.

The term "osteogenic" refers to the ability of a substance or material that can induce bone formation.

"Osteoinductive", as used herein, refers to the quality of being able to recruit cells (e.g., osteoblasts) from the host that have the potential to stimulate new bone formation. In general, osteoinductive materials are capable of inducing heterotopic ossification, that is, bone formation in extraskeletal soft tissues (e.g., muscle).

The term "osteoimplant" is used herein in its broadest sense and is not intended to be limited to any particular shapes, sizes, configurations, compositions, or applications. Osteoimplant refers to any device or material for implantation that aids or augments bone formation or healing. Osteoimplants are often applied at a bone defect site, e.g., one resulting from injury, defect brought about during the course of surgery, infection, malignancy, inflammation, or developmental malformation. Osteoimplants can be used in a variety of orthopedic, neurosurgical, dental, and oral and maxillofacial surgical procedures such as the repair of simple and compound fractures and non-unions, external, and internal fixations, joint reconstructions such as arthrodesis, general arthroplasty, deficit filling, disectomy, laminectomy, anterior cerival and thoracic operations, spinal fusions, etc.

The term "penetrate" refers to the ability of one substance to invade or infiltrate another. Penetrate may refer to complete or partial penetration. A polymer may infiltrate the particles of the composite. That is, the polymer may infiltrate the voids, gaps, holes, pores, crevices, etc. of the particles. After implantation, cells, tissue, or bone may invade the implanted composite.

The term "plasticizer", as used herein, refers to an additive that softens hard polymers or plastics. The plasticizer makes the polymer formable or flexible. Plasticizers are thought to work by embedding themselves between the chains of polymers, spacing them apart, and thus lowering the glass transition temperature. Preferably, the plasticizers used in the inventive composites are non-toxic and biocompatible. In certain embodiments, as the plasticizer diffuses out of the composite osteoimplant the composite loses its formability.

The terms "polynucleotide", "nucleic acid", or "oligonucleotide" refer to a polymer of nucleotides. The terms "polynucleotide", "nucleic acid", and "oligonucleotide", may be used interchangeably. Typically, a polynucleotide comprises at least three nucleotides. DNAs and RNAs are exemplary polynucleotides. The polymer may include natural nucleosides (i.e., adenosine, thymidine, guanosine, cytidine, uridine, deoxyadenosine, deoxythymidine, deoxyguanosine, and deoxycytidine), nucleoside analogs (e.g., 2-aminoadenosine, 2-thithymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), chemically modified bases, biologically modified bases (e.g., methylated bases), intercalated bases, modified sugars (e.g., 2'-fluororibose, ribose, 2'-deoxyriboses, arabinose, and hexose), or modified phosphate groups (e.g., phosphorothioates and 5'-N-phosphoramidite linkages). The polymer may also be a short strand of nucleic acids such as RNAi, siRNA, or shRNA.

As used herein, a "polypeptide", "peptide", or "protein" includes a string of at least three amino acids linked together by peptide bonds. The terms "polypeptide", "peptide", and "protein", may be used interchangeably. In some embodiments, peptides may contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide may be modified, for example, by the addition of a chemical entity such as a carbohydrate group, a phosphate group, a farnesyl group, an isofarnesyl group, a fatty acid group, a linker for conjugation, functionalization, or other modification, etc. In one embodiment, the modifications of the peptide lead to a more stable peptide (e.g., greater half-life in vivo). These modifications may include cyclization of the peptide, the incorporation of D-amino acids, etc. None of the modifications should substantially interfere with the desired biological activity of the peptide.

The terms "polysaccharide" or "oligosaccharide", as used herein, refer to any polymer or oligomer of carbohydrate residues. The polymer or oligomer may consist of anywhere from two to hundreds to thousands of sugar units or more. "Oligosaccharide" generally refers to a relatively low molecular weight polymer, while "polysaccharide" typically refers to a higher molecular weight polymer. Polysaccharides may be purified from natural sources such as plants or may be synthesized de novo in the laboratory. Polysaccharides isolated from natural sources may be modified chemically to change their chemical or physical properties (e.g., reduced, oxidized, phosphorylated, cross-linked). Carbohydrate polymers or oligomers may include natural sugars (e.g., glucose, fructose, galactose, mannose, arabinose, ribose, xylose, etc.) and/or modified sugars (e.g., 2'-fluororibose, 2'-deoxyribose, etc.). Polysaccharides may also be either straight or branched. They may contain both natural and/or unnatural carbohydrate residues. The linkage between the residues may be the typical ether linkage found in nature or may be a linkage only available to synthetic chemists. Examples of polysaccharides include cellulose, maltin, maltose, starch, modified starch, dextran, poly(dextrose), and fructose. Glycosaminoglycans are also considered polysaccharides. Sugar alcohol, as used herein, refers to any polyol such as sorbitol, mannitol, xylitol, galactitol, erythritol, inositol, ribitol, dulcitol, adonitol, arabitol, dithioerythritol, dithiothreitol, glycerol, isomalt, and hydrogenated starch hydrolysates.

The term "porogen" refers to a chemical compound that may be part of the inventive composite and upon implantation or prior to implantation diffuses, dissolves, and/or degrades to leave a pore in the osteoimplant composite. The porogen may be introduced into the composite during manufacture, during preparation of the composite (e.g., in the operating room), or after implantation. The porogen essentially reserves space in the composite while the composite is being molded but once the composite is implanted the porogen diffuses, dissolves, or degrades, thereby inducing porosity into the composite. In this way the porogen provides latent pores. In certain embodiments, the porogen may also be leached out of the composite before implantation. This resulting porosity of the implant generated during manufacture or after implantation (i.e., "latent porosity") is thought to allow infiltration by cells, bone formation, bone remodeling, osteoinduction, osteoconduction, and/or faster degradation of the osteoimplant. A porogen may be a gas (e.g., carbon dioxide, nitrogen, or other inert gas), liquid (e.g., water, biological fluid), or solid. Porogens are typically water soluble such as salts, sugars (e.g., sugar alcohols), polysaccharides (e.g., dextran (poly(dextrose)), water soluble small molecules, etc. Porogen can also be natural or synthetic polymers, oligomers, or monomers that are water soluble or degrade quickly under physiological conditions. Exemplary polymers include polyethylene glycol, poly(vinylpyrollidone), pullulan, poly(glycolide), poly(lactide), poly(lactide-co-glycolide), other polyesters, and starches.

The term "porosity" refers to the average amount of non-solid space contained in a material (e.g., a composite of the present invention). The porosity of a composite can be defined as the ratio of the total volume of the pores (i.e., void volume) in the material to the overall volume of the composite. Porosity may in certain embodiments refer to "latent porosity" wherein pores are only formed upon diffusion, dissolution, or degradation of a material occupying the pores. The pores in such an instance may be formed after implantation.

As used herein, the term "remodeling" describes the process by which native bone, processed bone allograft, whole bone sections employed as grafts, and other bony tissues are replaced with new cell-containing host bone tissue by the action of osteoclasts and osteoblasts. Remodeling also describes the process by which non-bony native tissue and tissue grafts are removed and replaced with new, cell-containing tissue in vivo. Remodeling also describes how inorganic materials (e.g., calcium-phosphate materials, such as β-tricalcium phosphate) is replaced with living bone.

As used herein, the term "settable" refers to a material that may be rendered more resistant to mechanical deformation as compared to a formable state.

As used herein, the term "set" refers to the state of a material that has been rendered more resistant to mechanical deformation with respect to a formable state.

The term "shaped" as used to characterize a material (e.g., composite) or an osteoimplant refers to a material or osteoimplant of a determined or regular form or configuration in contrast to an indeterminate or vague form or configuration (as in the case of a lump or other solid matrix of special form). The material may be shaped into any shape, configuration, or size. Materials can be shaped as sheets, blocks, plates, disks, cones, pins, screws, tubes, teeth, bones, portions of bones, wedges, cylinders, threaded cylinders, and the like, as well as more complex geometric configurations.

As used herein, the term "small molecule" is used to refer to molecules, whether naturally-occurring or artificially created (e.g., via chemical synthesis), that have a relatively low molecular weight. Typically, small molecules have a molecular weight of less than about 2,500 g/mol, more preferably less than 1000 g/mol. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by an appropriate governmental agency or body (e.g., the U.S. Food and Drug Administration).

As used herein, the term "transformation" describes the process by which a material is removed from an implant site and replaced by host tissue after implantation. Transformation may be accomplished by a combination of processes, including but not limited to remodeling, degradation, resorption, and tissue growth and/or formation. Removal of the material may be cell-mediated or accomplished through chemical processes, such as dissolution and hydrolysis.

DETAILED DESCRIPTION OF CERTAIN PREFERRED EMBODIMENTS

The present invention stems from the recognition that it would be useful to have bone substitute material that is sufficiently moldable or flowable to administer to a subject by injecting or molding the composite into an irregularly shaped implantation site (e.g., a bone defect, a void, or a fracture). The composite may be made moldable or flowable before administration such as by heating the composite or combining the composite with a suitable solvent. The viscosity of the resulting composite may range from a thick, flowable liquid (for example, like molasses or honey) to a moldable, dough-like putty. In certain embodiments, the composite is naturally moldable or flowable and is set by exposing the composite to predetermined conditions (e.g., cooling, UV irradiation, IR irradiation, microwave irradiation). The invention also provides methods of preparing and using the inventive composite as well as kits for administering the inventive composite. In one embodiment, bone-derived tissue or other particulate material is combined with a polymer and injected, extruded, molded, or similarly delivered to a tissue site (e.g., bony defect) of a subject. The inventive composite is engineered to set in situ to form a solid composite that has a desired mechanical strength. In certain embodiments, the polymer may include monomers or pre-polymers, or it may be a polymer that has been rendered formable by heating it above its glass transition temperature or melting point, or through combination with a solvent.

Particulate Component of Composite
Bone-Derived Material

Any type of particles comprising inorganic material, bone substitute material, bone-derived material, or combinations or composites thereof may be utilized in the present invention. In certain embodiments, a bone-derived material is used in the inventive composites. In one embodiment, bone particles employed in the preparation of the bone particle-containing composite are obtained from cortical, cancellous, and/or corticocancellous bone. The bone-derived material may be derived from any vertebrate. The bone-derived material may be of autogenous, allogenic, and/or xenogeneic origin. In certain embodiments, the bone-derived material is autogenous, that is, the bone-derived material is from the subject being treated. In other embodiments, the bone-derived material is allogenic (e.g., from donors). Preferably, the source of the bone is matched to the eventual recipient of the inventive composite (i.e., the donor and recipient are preferably of the same species). For example, human bone-derived material is typically used in a human subject. In certain particular embodiments, the bone particles are obtained from cortical bone of allogenic origin. In certain embodiments, the bone-derived material is obtained from bone of xenogeneic origin. Porcine and bovine bone are particularly advantageous types of xenogeneic bone tissue that can be used individually or in combination as sources for the bone-derived material. Xenogenic bone tissue may be combined with allogenic or autogenous bone.

Particles of bone-derived material are formed by any process known to break down bone into small pieces. Exemplary processes for forming such particles include milling whole bone to produce fibers, chipping whole bone, cutting whole bone, grinding whole bone, fracturing whole bone in liquid nitrogen, or otherwise disintegrating the bone tissue. Particles can optionally be sieved to produce particles of a specific size range. The particles may be of any shape or size. Exemplary shapes include spheroidal, plates, fibers, cuboidal, sheets, rods, oval, strings, elongated particles, wedges, discs, rectangular, polyhedral, etc. In some embodiments, particles may be between about 10 microns and about 1000 microns in diameter or more. In some embodiments, particles may be between about 20 microns and about 800 microns in diameter or more. In certain embodiments, the particles range in size from approximately 100 microns in diameter to approximately 500 microns in diameter. In certain embodiments, the particles range in size from approximately 300 microns in diameter to approximately 800 microns in diameter. As for irregularly shaped particles, the recited dimension ranges may represent the length of the greatest or smallest dimension of the particle. As will be appreciated by one of skill in the art, for injectable composites, the maximum particle size will depend in part on the size of the cannula or needle through which the material will be delivered In certain embodiments, the particle size distribution of the particles that are combined with a polymer to form the inventive composite with respect to a mean value may be plus or minus, e.g., about 10% or less of the mean value, about 20% or less of the mean value, about 30% or less of the mean value, about 40% or less of the mean value, about 50% or less of the mean value, about 60% or less of the mean value, about 70% or less of the mean value, about 80% or less of the mean value, or about 90% or less of the mean value. In other embodiments, the particle size distribution of the particles that are combined with a polymer to form the inventive composite with respect to a median value may be plus or minus, e.g., about 10% or less of the median value, about 20% or less of the median value, about 30% or less of the median value, about 40% or less of the median value, about 50% or less of the median value, about 60% or less of the median value, about 70% or less of the median value, about 80% or less of the median value, or about 90% or less of the median value. In certain embodiments, at least about 60, 70, or 80 weight percent of the particles posses a median length of about 10 microns to about 1000 microns in their greatest dimension. In certain embodiments, at least about 60, 70, or 80 weight percent of the particles posses a median length of about 20 microns to about 800 microns in their greatest dimension. For particles that are fibers or other elongated particles, at least about 60 weight percent, at least about 70 weight percent, or at least about 80 weight percent of the particles possess a median length of from about 2 to about 200 mm, or more preferably from about 10 to about 100 mm, a median thickness of from about 0.05 to about 2 mm, and preferably from about 0.2 to about 1 mm, and a median width of from about 1 mm to about 20 mm and preferably from about 2 to about 5 mm. The particles may possess a median length to median thickness ratio from at least about 5:1 up to about 500:1, preferably from at least about 50:1 up to about 500:1, or more and preferably from about 50:1 up to about 100:1; and a median length to median width ratio of from about 10:1 to about 200:1 and preferably from about 50:1 to about 100:1. In certain embodiments, the bone-derived particles are short fibers having a cross-section of about 300 microns to about 100 microns and a length of about 1 mm to about 4 mm.

The processing of the bone to provide the particles may be adjusted to optimize for the desired size and/or distribution of the particles. The desired properties of the resulting inventive composite (e.g., mechanical properties) may also be engineered by adjusting the weight percent, shapes, sizes, distribution, etc. of the bone-derived particles or other particles. For example, an inventive composite may be made more viscous by including a higher percentage of particles.

The bone-derived particles utilized in accordance with the present invention may be demineralized, non-demineralized, mineralized, or anorganic. In certain embodiments, the resulting bone-derived particles are used "as is" in preparing the inventive composites. In other embodiments, the particles are defatted and disinfected. An exemplary defatting/disinfectant solution is an aqueous solution of ethanol. Other organic solvent may also be used in the defatting and disinfecting the particles. For example, methanol, isopropanol, butanol, DMF, DMSO, diethyl ether, hexanes, glyme, tetrahydrofuran, chloroform, methylene chloride, and carbon tetrachloride may be used. In certain embodiments, a non-halogenated solvent is used. The defatting/disinfecant solution may also include a detergent (e.g., an aqueous solution of a detergent). Ordinarily, at least about 10 to about 40 percent by weight of water (i.e., about 60 to about 90 weight percent of defatting agent such as alcohol) should be present in the defatting/disinfecting solution to produce optimal lipid removal and disinfection within the shortest period of time. An exemplary concentration range of the defatting solution is from about 60 to about 85 weight percent alcohol, for example, about 70 weight percent alcohol.

In certain embodiments, the particles are demineralized. The bone-derived particles are optionally demineralized in accordance with known and/or conventional procedures in order to reduce their inorganic mineral content. Demineralization methods remove the inorganic mineral component of bone by employing acid solutions. Such methods are well known in the art, see for example, Reddi, et al., *Proc. Nat. Acad. Sci.*, 1972, 69:1601-1605, the contents of which are incorporated herein by reference. The strength of the acid solution, the shape and dimensions of the bone particles and the duration of the demineralization treatment will determine the extent of demineralization. Reference in this regard is made to Lewandrowski, et al., *J. Biomed. Mater. Res.*, 1996, 31:365-372 and U.S. Pat. No. 5,290,558, the contents of both of which are incorporated herein by reference.

In an exemplary defatting/disinfecting/demineralization procedure, the bone particles are subjected to a defatting/disinfecting step, followed by an acid demineralization step. An exemplary defatting/disinfectant solution is an aqueous solution of ethanol. Ordinarily, at least about 10 to about 40 percent by weight of water (i.e., about 60 to about 90 weight percent of defatting agent such as alcohol) should be present in the defatting/disinfecting solution to produce optimal lipid removal and disinfection within a reasonable period of time. An exemplary concentration range of the defatting solution is from about 60 to about 85 weight percent alcohol, for example, about 70 weight percent alcohol. Ethanol is typically the alcohol used in this step; however, other alcohols such as methanol, propanol, isopropanol, denatured ethanol, etc. may also be used. Following defatting, the bone particles are immersed in acid over time to effect their demineralization. The acid also disinfects the bone by killing viruses, vegetative microorganisms, and spores. Acids which can be employed in this step include inorganic acids such as hydrochloric acid and organic acids such as peracetic acid. After acid treatment, the demineralized bone particles are rinsed with sterile water to remove residual amounts of acid and thereby raise the pH. The bone particles may be dried, for example, by lyophilization, before being incorporated into the composite. The bone particles may be stored under aseptic conditions, for example, in a lyophilized state, until they are used or sterilized using known methods (e.g., gamma irradiation) shortly before combining them with a polymer.

As utilized herein, the phrase "superficially demineralized" as applied to the bone particles refers to bone particles possessing at least about 90% by weight of their original inorganic mineral content. The phrase "partially demineralized" as applied to the bone particles refers to bone particles possessing from about 8% to about 90% weight of their original inorganic mineral content, and the phrase "fully demineralized" as applied to the bone particles refers to bone particles possessing less than about 8%, preferably less than about 1%, by weight of their original inorganic mineral content. The unmodified term "demineralized" as applied to the bone particles is intended to cover any one or combination of the foregoing types of demineralized bone particles, that is, superficially demineralized, partially demineralized, or fully demineralized bone particles.

In an alternative embodiment, surfaces of bone particles may be lightly demineralized according to the procedures in our commonly owned U.S. patent application Ser. No. 10/285,715, filed Nov. 1, 2002, published as U.S. Patent Publication No. 2003/0144743, on Jul. 31, 2003, the contents of which are incorporated herein by reference. Even minimal demineralization, for example, of less than 5% removal of the inorganic phase, increases the hydroxylation of bone fibers and the surface concentration of amine groups. Demineralization may be so minimal, for example, less than 1%, that the removal of the calcium phosphate phase is almost undetectable. Rather, the enhanced surface concentration of reactive groups defines the extent of demineralization. This may be measured, for example, by titrating the reactive groups. In one embodiment, in a polymerization reaction that utilizes the exposed allograft surfaces to initiate a reaction, the amount of unreacted monomer remaining may be used to estimate reactivity of the surfaces. Surface reactivity may be assessed by a surrogate mechanical test, such as a peel test of a treated coupon of bone adhering to a polymer.

In certain embodiments, the bone-derived particles are subjected to a process that partially or totally removes their initial organic content to yield mineralized and anorganic bone particles, respectively. Different mineralization methods have been developed and are known in the are (Hurley et al., *Milit. Med.* 1957, 101-104; Kershaw, *Pharm. J.* 6:537, 1963; and U.S. Pat. No. 4,882,149; each of which is incorporated herein by reference). For example, a mineralization procedure can include a de-greasing step followed by a basic treatment (with ammonia or another amine) to degrade residual proteins and a water washing (U.S. Pat. Nos. 5,417,975 and 5,573,771; both of which are incorporated herein by reference). Another example of a mineralization procedure includes a defatting step where bone particles are sonicated in 70% ethanol for 1-3 hours.

If desired, the bone-derived particles can be modified in one or more ways, e.g., their protein content can be augmented or modified as described, for example, in U.S. Pat. Nos. 4,743,259 and 4,902,296, the contents of both of which are incorporated herein by reference.

Mixtures or combinations of one or more of the foregoing types of bone-derived particles can be employed. For example, one or more of the foregoing types of demineralized bone-derived particles can be employed in combination with non-demineralized bone-derived particles, i.e., bone-derived particles that have not been subjected to a demineralization process, or inorganic materials. The amount of each individual type of bone-derived particle employed can vary widely depending on the mechanical and biological properties desired. Thus, mixtures of bone-derived particles of various shapes, sizes, and/or degrees of demineralization may be assembled based on the desired mechanical, thermal, chemical, and biological properties of the composite. A desired balance between the various properties of the composite (e.g., a balance between mechanical and biological properties) may be achieved by using different combinations of particles. Suitable amounts of various particle types can be readily determined by those skilled in the art on a case-by-case basis by routine experimentation.

The differential in strength, osteogenicity, and other properties between partially and fully demineralized bone-derived particles on the one hand, and non-demineralized, superficially demineralized bone-derived particles, inorganic ceramics, and bone substitutes on the other hand can be exploited. For example, in order to increase the compressive strength of the osteoimplant, the ratio of nondemineralized and/or superficially demineralized bone-derived particles to partially or fully demineralized bone-derived particles may favor the former, and vice versa. The bone-derived particles in the composite also play a biological role. Non-demineralized bone-derived particles bring about new bone in-growth by osteoconduction. Demineralized bone-derived particles likewise play a biological role in bringing about new bone in-growth by osteoinduction. Both types of bone-derived particles are gradually remodeled and replaced by new host bone as degradation of the composite progresses over time. Thus, the use of various types of bone particles can be used to control the overall mechanical and biological properties, i.e., the strength, osteoconductivity, and/or osteoinductivity, etc., of the osteoimplant.

Surface Modification of Bone-Derived Particles

The bone-derived particles may be optionally treated to enhance their interaction with the polymer of the composite or to confer some property to the particle surface. While some bone-derived particles will interact readily with the monomer and be covalently linked to the polymer matrix, it may be desirable to modify the surface of the bone-derived particles to facilitate incorporation into polymers that do not bond well to bone, such as poly(lactides). Surface modification may provide a chemical substance that is strongly bonded to the surface of the bone, e.g., covalently bonded to the surface. The bone-derived particles may also be coated with a material to facilitate interaction with the polymer of the composite.

In one embodiment, silane coupling agents are employed to link a monomer or initiator molecule to the surface of the bone-derived particles. The silane has at least two sections, a set of three leaving groups and an active group. The active group may be connected to the silicon atom in the silane by an elongated tether group. An exemplary silane coupling agent is 3-trimethoxysilylpropylmethacrylate, available from Union Carbide. The three methoxy groups are the leaving groups, and the methacrylate active group is connected to the silicon atom by a propyl tether group. In one embodiment, the leaving group is an alkoxy group such as methoxy or ethoxy. Depending on the solvent used to link the coupling agent to the bone-derived particle, hydrogen or alkyl groups such as methyl or ethyl may serve as the leaving group. The length of the tether determines the intimacy of the connection between the polymer matrix and the bone-derived particle. By providing a spacer between the bone-derived particle and the active group, the tether also reduces competition between chemical groups at the particle surface and the active group and makes the active group more accessible to the monomer during polymerization.

In one embodiment, the active group is an analog of the monomer of the polymer used in the composite. For example, amine active groups will be incorporated into polyamides, polyesters, polyurethanes, polycarbonates, polycaprolactone, and other polymer classes based on monomers that react with amines, even if the polymer does not contain an amine. Hydroxy-terminated silanes will be incorporated into polyamino acids, polyesters, polycaprolactone, polycarbonates, polyurethanes, and other polymer classes that include hydroxylated monomers. Aromatic active groups or active groups with double bonds will be incorporated into vinyl polymers and other polymers that grow by radical polymerization (e.g., polyacrylates, polymethacrylates). It is not necessary that the active group be monofunctional. Indeed, it may be preferable that active groups that are to be incorporated into polymers via step polymerization be difunctional. A silane having two amines, even if one is a secondary amine, will not terminate a polymer chain but can react with ends of two different polymer chains. Alternatively, the active group may be branched to provide two reactive groups in the primary position.

An exemplary list of silanes that may be used with the invention is provided in U.S. Patent Publication No. 2004/0146543, the contents of which are incorporated herein by reference. Silanes are available from companies such as Union Carbide, AP Resources Co. (Seoul, South Korea), and BASF. Where the silane contains a potentially non-biocompatible moiety as the active group, it should be used to tether a biocompatible compound to the bone particle using a reaction in which the non-biocompatible moiety is the leaving group. It may be desirable to attach the biocompatible compound to the silane before attaching the silane to the bone-derived particle, regardless of whether the silane is biocompatible or not. The derivatized silanes may be mixed with silanes that can be incorporated directly into the polymer and reacted with the bone-derived particles, coating the bone particles with a mixture of "bioactive" silanes and "monomer" silanes. U.S. Pat. No. 6,399,693, the contents of which are incorporated herein by reference discloses composites of silane modified polyaromatic polymers and bone. Silane-derivatized polymers may be used in the inventive composites instead of or in addition to first silanizing the bone-derived particles.

The active group of the silane may be incorporated directly into the polymer or may be used to attach a second chemical group to the bone particle. For example, if a particular monomer polymerizes through a functional group that is not commercially available as a silane, the monomer may be attached to the active group.

Non-silane linkers may also be employed to produce composites according to the invention. For example, isocyanates will form covalent bonds with hydroxyl groups on the surface of hydroxyapatite ceramics (de Wijn, et al., "Grafting PMMA on Hydroxyapatite Powder Particles using Isocyanatoethylmethacrylate," Fifth World Biomaterials Congress, May 29-Jun. 2, 1996, Toronto, Calif.). Isocyanate anchors, with tethers and active groups similar to those described with respect to silanes, may be used to attach monomer-analogs to the bone particles or to attach chemical groups that will link covalently or non-covalently with a polymer side group. Polyamines, organic compounds containing one or more primary, secondary, or tertiary amines, will also bind with both the bone particle surface and many monomer and polymer side groups. Polyamines and isocyanates may be obtained from Aldrich.

Alternatively, a biologically active compound such as a biomolecule, a small molecule, or a bioactive agent may be attached to the bone-derived particle through the linker. For example, mercaptosilanes will react with the sulfur atoms in proteins to attach them to the bone-derived particle. Aminated, hydroxylated, and carboxylated silanes will react with a wide variety functional groups. Of course, the linker may be optimized for the compound being attached to the bone-derived particle.

Biologically active molecules can modify non-mechanical properties of the composite as it is degraded. For example, immobilization of a drug on the bone particle allows it to be gradually released at an implant site as the composite is degraded. Anti-inflammatory agents embedded within the composite will control the inflammatory response long after the initial response to injection of the composite. For example, if a piece of the composite fractures several weeks after injection, immobilized compounds will reduce the intensity of any inflammatory response, and the composite will continue to degrade through hydrolytic or physiological processes. Compounds may also be immobilized on the bone-derived particles that are designed to elicit a particular metabolic response or to attract cells to the injection site.

Some biomolecules, small molecules, and bioactive agents may also be incorporated into the polymer used in the composite. For example, many amino acids have reactive side chains. The phenol group on tyrosine has been exploited to form polycarbonates, polyarylates, and polyiminocarbonates (see Pulapura, et al., "Tyrosine-derived polycarbonates: Backbone-modified "pseudo"-poly(amino acids) designed for biomedical applications," *Biopolymers*, 1992, 32: 411-417; and Hooper, et al., "Diphenolic monomers derived from the natural amino acid α-L-tyrosine: an evaluation of peptide coupling techniques," *J. Bioactive and Compatible Polymers*, 1995, 10:327-340, the entire contents of both of which are incorporated herein by reference). Amino acids such as lysine, arginine, hydroxylysine, proline, and hydroxyproline also have reactive groups and are essentially tri-functional. Amino acids such as valine, which has an isopropyl side chain, are still difunctional. Such amino acids may be attached to the silane and still leave one or two active groups available for incorporation into a polymer.

Non-biologically active materials may also be attached to the bone particles. For example, radioopaque, luminescent, or magnetically active particles may be attached to the bone particles using the techniques described above. If a material, for example, a metal atom or cluster, cannot be produced as a silane or other group that reacts with calcium phosphate ceramics, then a chelating agent may be immobilized on the bone particle surface and allowed to form a chelate with the atom or cluster. As the bone is resorbed, these non-biodegradable materials are still removed from the tissue site by natural metabolic processes, allowing the degradation of the polymer and the resorption of the bone-derived particles to be tracked using standard medical diagnostic techniques.

In an alternative embodiment, the bone-derived particle surface is chemically treated before being derivatized or combined with a polymer. For example, non-demineralized bone-derived particles may be rinsed with phosphoric acid, e.g., for 1 to 15 minutes in a 5-50% solution by volume. Those skilled in the art will recognize that the relative volume of bone particles and phosphoric acid solution (or any other solution used to treat the bone particles), may be optimized depending on the desired level of surface treatment. Agitation will also increase the uniformity of the treatment both along individual particles and across an entire sample of particles. The phosphoric acid solution reacts with the mineral component of the bone to coat the particles with calcium phosphate, which may increase the affinity of the surface for inorganic coupling agents such as silanes and for the polymer component of the composite. As noted above, the surface may be partially demineralized to expose the collagen fibers at the particle surface.

The collagen fibers exposed by demineralization are typically relatively inert but have some exposed amino acid residues that can participate in reactions. The collagen may be rendered more reactive by fraying the triple helical structure of the collagen to increase the exposed surface area and the number of exposed amino acid residues. This not only increases the surface area available for chemical reactions but also for mechanical interaction with the polymer as well. Rinsing the partially demineralized bone particles in an alkaline solution will fray the collagen fibrils. For example, bone particles may be suspended in water at a pH of about 10 for about 8 hours, after which the solution is neutralized. One skilled in the art will recognize that this time period may be increased or decreased to adjust the extent of fraying. Agitation, for example, in an ultrasonic bath, may reduce the processing time. Alternatively, the particles may be sonicated with water, surfactant, alcohol, or some combination of these.

Alternatively, the collagen fibers may be cross-linked. A variety of cross-linking techniques suitable for medical applications are well known in the art (see, for example, U.S. Pat. No. 6,123,781, the contents of which are incorporated herein by reference). For example, compounds like 1-ethyl-3-(3-dimethylaminopropyl) carbodiimide hydrochloride, either alone or in combination with N-hydroxysuccinimide (NHS) will crosslink collagen at physiologic or slightly acidic pH (e.g., in pH 5.4 MES buffer). Acyl azides and genipin, a naturally occurring bicyclic compound including both carboxylate and hydroxyl groups, may also be used to cross-link collagen chains (see Simmons, et al, "Evaluation of collagen cross-linking techniques for the stabilization of tissue matrices," *Biotechnol. Appl. Biochem.,* 1993, 17:23-29; PCT Publication WO98/19718, the contents of both of which are incorporated herein by reference). Alternatively, hydroxymethyl phosphine groups on collagen may be reacted with the primary and secondary amines on neighboring chains (see U.S. Pat. No. 5,948,386, the entire contents of which are incorporated herein by reference). Standard cross-linking agents such as mono- and dialdehydes, polyepoxy compounds, tanning agents including polyvalent metallic oxides, organic tannins, and other plant derived phenolic oxides, chemicals for esterification of carboxyl groups followed by reaction with hydrazide to form activated acyl azide groups, dicyclohexyl carbodiimide and its derivatives and other heterobifunctional crosslinking agents, hexamethylene diisocyanate, and sugars may also be used to cross-link the collagen. The bone-derived particles are then washed to remove all leachable traces of the material. Enzymatic cross-linking agents may also be used. Additional cross-linking methods include chemical reaction, irradiation, application of heat, dehydrothermal treatment, enzymatic treatment, etc. One skilled in the art will easily be able to determine the optimal concentrations of cross-linking agents and incubation times for the desired degree of cross-linking.

Both frayed and unfrayed collagen fibers may be derivatized with monomer, pre-polymer, oligomer, polymer, initiator, and/or biologically active or inactive compounds, including but not limited to biomolecules, bioactive agents, small molecules, inorganic materials, minerals, through reactive amino acids on the collagen fiber such as lysine, arginine, hydroxylysine, proline, and hydroxyproline. Monomers that link via step polymerization may react with these amino acids via the same reactions through which they polymerize. Vinyl monomers and other monomers that polymerize by chain polymerization may react with these amino acids via their reactive pendant groups, leaving the vinyl group free to polymerize. Alternatively, or in addition, bone-derived particles may be treated to induce calcium phosphate deposition and crystal formation on exposed collagen fibers. Calcium ions may be chelated by chemical moieties of the collagen fibers, and/or calcium ions may bind to the surface of the collagen fibers. James et al., *Biomaterials* 20:2203-2313, 1999; incorporated herein by reference. The calcium ions bound to the to the collagen provides a biocompatible surface, which allows for the attachment of cells as well as crystal growth. The polymer will interact with these fibers, increasing interfacial area and improving the wet strength of the composite.

Additionally or alternatively, the surface treatments described above or treatments such as etching may be used to increase the surface area or surface roughness of the bone-derived particles. Such treatments increase the interfacial strength of the particle/polymer interface by increasing the surface area of the interface and/or the mechanical interlocking of the bone-derived particles and the polymer. Such surface treatments may also be employed to round the shape or smooth the edges of bone particles to facilitate delivery of the inventive composite. Such treatment is particularly useful for injectable composites.

In some embodiments, surface treatments of the bone-derived particles are optimized to enhance covalent attractions between the bone-derived particles and the polymer of the composite. In an alternative embodiment, the surface treatment may be designed to enhance non-covalent interactions between the bone-derived particle and the polymer matrix. Exemplary non-covalent interactions include electrostatic interactions, hydrogen bonding, pi-bond interactions, hydrophobic interactions, van der Waals interactions, and mechanical interlocking. For example, if a protein or a polysaccharide is immobilized on the bone-derived particle, the chains of the polymer will become physically entangled with the long chains of the biological polymer when they are combined. Charged phosphate sites on the surface of the particles, produced by washing the bone particles in basic solution, will interact with the amino groups present in many biocompatible polymers, especially those based on amino acids. The pi-orbitals on aromatic groups immobilized on a bone-derived particle will interact with double bonds and aromatic groups of the polymer.

Additional Particulate Materials

Inorganic materials, including, but not limited, calcium phosphate materials and bone substitute materials, may also be exploited for use as particulate inclusions in the inventive composites. Exemplary inorganic inorganics for use with the invention include aragonite, dahlite, calcite, amorphous calcium carbonate, vaterite, weddellite, whewellite, struvite, urate, ferrihydrite, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, and BIOGLASS™, a calcium phosphate silica glass available from U.S. Biomaterials Corporation. Substituted calcium phosphate phases are also contemplated for use with the invention, including but not limited to fluorapatite, chlorapatite, magnesium-substituted tricalcium phosphate, and carbonate hydroxyapatite. In certain embodiments, the inorganic material is a substituted form of hydroxyapatite. For example, the hydroxyapatite may be substituted with other ions such as fluoride, chloride, magnesium, sodium, potassium, etc. Additional calcium phosphate phases suitable for use with the invention include those disclosed in U.S. Patents RE 33,161 and RE 33,221 to Brown et al.; U.S. Pat. Nos. 4,880,610; 5,034,059; 5,047,031; 5,053,212; 5,129,905; 5,336,264; and U.S. Pat. No. 6,002,065 to Constantz et al.; U.S. Pat. Nos. 5,149,368; 5,262,166 and 5,462,722 to Liu et al.; U.S. Pat. Nos. 5,525,148 and 5,542,973 to Chow et al., U.S. Pat. Nos. 5,717,006 and 6,001,394 to Daculsi et al., U.S. Pat. No. 5,605,713 to Boltong et al., U.S. Pat. No. 5,650,176 to Lee et al., and U.S. Pat. No. 6,206,957 to Driessens et al, and biologically-derived or biomimetic materials such as those identified in Lowenstam H A, Weiner S, *On Biomineralization*, Oxford University Press, 1989; each of which is incorporated herein by reference.

In another embodiment, a particulate composite material may be employed in the mixture with the polymer. For example, inorganic materials such as those described above or bone-derived materials may be combined with proteins such as bovine serum albumin (BSA), collagen, or other extracellular matrix components to form a composite. Alternatively or in addition, inorganic materials or bone-derived materials may be combined with synthetic or natural polymers to form a composite using the techniques described in our co-pending U.S. patent applications, U.S. Ser. No. 10/735,135, filed Dec. 12, 2003; U.S. Ser. No. 10/681,651, filed Oct. 8, 2003; and U.S. Ser. No. 10/639,912, filed Aug. 12, 2003, the contents of all of which are incorporated herein by reference. These composites may be partially demineralized as described herein to expose the organic material at the surface of the composite before they are combined with a polymer.

In certain embodiments, the particular composite material is one described in U.S. patent applications, U.S. Ser. No. 10/771,736, filed Feb. 2, 2004, and published as US 2005/0027033; and U.S. Ser. No. 11/336,127, filed Jan. 19, 2006, and published as US 2006/0216323; each of which is incorporated herein by reference. Composite materials described in these applications include a polyurethane matrix and a reinforcement embedded in the matrix. The polyurethane matrix may be formed by reaction of a polyisocyanate (e.g., lysine diisocyanate, toluene diisocyanate, arginine diisocyanate, asparagine diisocyanate, glutamine diisocyanate, hexamethylene diisocyanate, hexane diisocyanate, methylene bis-p-phenyl diisocyanate, isocyanurate polyisocyanates, 1,4-butane diisocyanate, uretdione polyisocyanate, or aliphatic, alicyclic, or aromatic polyisocyanates) with an optionally hydroxylated biomolecule (e.g., a phospholipids, fatty acid, cholesterol, polysaccharide, starch, or a combination or modified form of any of the above) to form a biodegradable polymer, while the reinforcement comprises bone-derived material or a bone substitute (e.g., calcium carbonate, calcium sulfate, calcium phosphosilicate, sodium phosphate, calcium aluminate, calcium phosphate, calcium carbonate, hydroxyapatite, demineralized bone, mineralized bone, or combinations or modified forms of any of these).

Particles of composite material for use in the present invention may contain between about 5 and about 80% of bone-derived or other inorganic material, for example, between about 60% and about 75%. Particulate materials for use in the inventive composites may be modified to increase the concentration of nucleophilic groups (e.g., amino or hydroxyl groups) at their surfaces using the techniques described herein.

The inventive composite may contain between about 5% and 80% by weight bone-derived particles, bone substitute particles, or inorganic material particles. In certain embodiments, the particles make up between about 10% and about 30% by weight of the composite. In certain embodiments, the particles make up between about 30% and about 50% by weight of the composite. In certain embodiments, the particles make up between about 40% and about 50% by weight of the composite. In certain embodiments, the particles make up between about 60% and about 75% by weight of the composite. In certain embodiments, the particles make up between about 45% and about 70% by weight of the composite. In certain embodiments, the particles make up between about 50% and about 65% by weight of the composite. In certain particular embodiments, the particles make up approximately 20%, 25%, 30%, or 40% by weight of the composite. In certain particular embodiments, the particles make up approximately 45%, 46%, 47%, 48%, 49%, 50%, 51%, 52%, 53%, 54%, 55%, 56%, 57%, 58%, 59%, 60%, 61%, 62%, 63%, 64%, or 65% by weight of the composite.

Combining the Particles with a Polymer

To form the inventive composite, the particles as discussed herein are combined with a polymer thereby forming a naturally moldable or flowable composite or a composite that can be made moldable or flowable. The polymer may be further modified by further cross-linking or polymerization after combination with particles to form a composite in which the polymer is covalently linked to the particles. In some embodiments, the polymer is a polymer/solvent mixture that hardens when the solvent is removed (e.g., when the solvent is allowed to evaporate or diffuse away). Exemplary solvents include but are not limited to alcohols (e.g., methanol, ethanol, propanol, butanol, hexanol, etc.), water, saline, DMF, DMSO, glycerol, and PEG. In certain embodiments, the solvent is a biological fluid such as blood, plasma, serum, marrow, etc. In certain embodiments, the inventive composite is heated above the melting or glass transition temperature of one or more of its components and becomes set after implantation as it cools. In certain embodiments, the inventive composite is set by exposing the composite to a heat source, or irradiating it with microwaves, IR rays, or UV light. The particles may also be mixed with a polymer that is sufficiently pliable to combine with the particles but that may require further treatment, for example, combination with a solvent or heating, to become a flowable or moldable composite.

In some embodiments, the composite is produced with a flowable polymer and then set in situ. For example, the cross-link density of a low molecular weight polymer may be increased by exposing it to electromagnetic radiation (e.g., UV light) or an alternative energy source. Alternatively, a photoactive cross-linking agent, chemical cross-linking agent, additional monomer, or combinations thereof may be mixed into the composite. Exposure to UV light after the mixture is injected into the implant site will increase one or both of the molecular weight and cross-link density, stiffening the polymer and thereby the composite. The polymer component of the composite may also be softened by a solvent, e.g., ethanol. If a biocompatible solvent is used, the polymer may be hardened in situ. As the composite sets, solvent leaving the composite is preferably released into the surrounding tissue without causing undesirable side effects such as irritation or an inflammatory response.

The polymer and the particulate phase may be combined by any method known to those skilled in the art. For example, a homogenous mixture of a polymer or polymer precursor and particles may be pressed together at ambient or elevated temperatures. At elevated temperatures, the process may also be accomplished without pressure. In some embodiments, the polymer or precursor is not held at a temperature of greater than approximately 60° C. for a significant time during mixing to prevent thermal damage to any biological component of the composite (e.g., bone-derived factors or cells). Alternatively or in addition, particles may be mixed or folded into a polymer softened by heat or a solvent. Alternatively, a formable polymer may be formed into a sheet that is then covered with a layer of particles. The particles may then be forced into the polymer sheet using pressure. In another embodiment, particles are individually coated with a polymer or polymer precursor, for example, using a tumbler, spray coater, or a fluidized bed, before being mixed with a larger quantity of polymer. This facilitates even coating of the particles and improves integration of the particles and polymer component of the composite.

Polymer processing techniques may also be used to combine the particles and a polymer or polymer precursor. For example, the polymer may be rendered formable, e.g., by heating or with a solvent, and combined with the particles by injection molding or extrusion forming. Alternatively, the polymer and particles may be mixed in a solvent and cast with or without pressure. The composite may be prepared from both formable and rigid polymers. For example, extrusion forming may be performed using pressure to manipulate a formable or rigid polymer.

In another embodiment, the particles may be mixed with a polymer precursor according to standard composite processing techniques. For example, regularly shaped particles may simply be suspended in a monomer. A polymer precursor may be mechanically stirred to distribute the particles or bubbled with a gas, preferably one that is oxygen- and moisture-free. Once the composite is mixed, it may be desirable to store it in a container that imparts a static pressure to prevent separation of the particles and the polymer precursor, which may have different densities. In some embodiments, the distribution and particle/polymer ratio may be optimized to produce at least one continuous path through the composite along the particles.

The interaction of the polymer component of the composite with the particles may also be enhanced by coating individual particles with a polymer precursor before combining them with bulk precursor. The coating enhances the association of the polymer component of the composite with the particles. For example, individual particles may be spray coated with a monomer or prepolymer. Alternatively, the individual particles may be coated using a tumbler—particles and a solid polymer material are tumbled together to coat the particles. A fluidized bed coater may also be used to coat the particles. In addition, the particles may simply be dipped into liquid or powdered polymer precursor. All of these techniques will be familiar to those skilled in the art.

In some embodiments, it may be desirable to infiltrate a polymer or polymer precursor into the vascular and/or interstitial structure of bone-derived particles or into the bone-derived tissue itself. The vascular structure of bone includes such structures such as osteocyte lacunae, Haversian canals, Volkmann's canals, canaliculi and similar structures. The interstitial structure of the bone particles includes the spaces between trabeculae and similar features. Many of the monomers and other polymer precursors suggested for use with the invention are sufficiently flowable to penetrate through the channels and pores of trabecular bone. Some may even penetrate into the trabeculae or into the mineralized fibrils of cortical bone. Thus, it may only be necessary to incubate the bone particles in neat monomer or other polymer precursor for a period of time to accomplish infiltration. In certain embodiments, the polymer itself is sufficiently flowable that it can penetrate the channels and pores of bone. The polymer may also be heated or combined with a solvent to make it more flowable for this purpose. Other ceramic materials or bone-substitute materials employed as a particulate phase may also include porosity that can be infiltrated as described herein.

Vacuum infiltration may be used to help a polymer or precursor infiltrate the lacunae and canals, and, if desired, the canaliculi. Penetration of the microstructural channels of the bone particles will maximize the surface area of the interface between the particles and the polymer and prevent solvents and air bubbles from being trapped in the composite, e.g., between trabeculae. Vacuum infiltration, where appropriate, will also help remove air bubbles from the inventive composite.

In another embodiment, infiltration may be achieved using solvent infiltration. Vacuum infiltration may be inappropriate for highly volatile monomers. Solvents employed for infiltration should carefully selected, as many of the most common solvents used for infiltration are toxic. Highly volatile solvents such as acetone will evaporate during infiltration, reducing the risk that they will be incorporated into the polymer and implanted into the subject. Exemplary solvents for use with the invention include but are not limited to dimethylsulfoxide (DMSO) and ethanol. As is well known to those skilled in the art, solvent infiltration is achieved by mixing the particles with solutions of the solvent with the polymer or polymer precursor, starting with very dilute solutions and proceeding to more concentrated solutions and finally to neat polymer or polymer precursor. Solvent infiltration can also provide improved tissue infiltration. In some embodiments, solvent infiltration is combined with pressure in vacuum; instead of finishing the infiltration with heat monomer, the pressure or vacuum is used to draw out the remaining solvent while pushing the polymer or polymer precursor even deeper into the particles.

One skilled in the art will recognize that other standard histological techniques, including pressure and heat, may be used to increase the infiltration of a polymer or polymer precursor into the particles. Infiltrated particles may then be combined with a volume of fresh polymer before administration. Automated apparatus for vacuum and pressure infiltration include the Tissue Tek VIP Vacuum infiltration processor E150/E300, available from Sakura Finetek, Inc.

Alternatively or in addition, a polymer or polymer precursor and particles may be supplied separately, e.g., in a kit, and mixed immediately prior to implantation or molding. The kit may contain a preset supply of bone-derived or other particles having, e.g., certain sizes, shapes, and levels of demineralization. The surface of the particles may have been optionally modified using one or more of the techniques described herein. Alternatively, the kit may provide several different types of particles of varying sizes, shapes, and levels of demineralization and that may have been chemically modified in different ways. A surgeon or other health care professional may also combine the components in the kit with autologous tissue derived during surgery or biopsy. For example, the surgeon may want to include autogenous tissue or cells, e.g., bone marrow or bone shavings generated while preparing the implant site, into the composite.

The composite may include practically any ratio of polymer component and particles, for example, between about 5 weight % bone and about 95 weight % particles. For example, the composite may include about 50% to about 70% by weight particles. The desired proportion may depend on factors such as the injection site, the shape and size of the particles, how evenly the polymer is distributed among the particles, desired flowability of the composite, desired handling of the composite, desired moldability of the composite, and the mechanical and degradation properties of the polymer matrix. The proportions of the polymer and particles can influence various characteristics of the composite, for example, its mechanical properties, including fatigue strength, the degradation rate, and the rate of biological incorporation. In addition, the cellular response to the composite will vary with the proportion of polymer and particles. In some embodiments, the desired proportion of particles may be determined not only by the desired biological properties of the injected material but by the desired mechanical properties of the injected material. That is, an increased proportion of particles will increase the viscosity of the composite, making it more difficult to inject or mold. A larger proportion of particles having a wide size distribution may give similar properties to a mixture having a smaller proportion of more evenly sized particles.

One skilled in the art will recognize that standard experimental techniques may be used to test these properties for a range of compositions to optimize a composite for a desired application. For example, standard mechanical testing instruments may be used to test the compressive strength and stiffness of the composite. Cells may be cultured on the composite for an appropriate period of time and the metabolic products and the amount of proliferation (e.g., the number of cells in comparison to the number of cells seeded) analyzed. The weight change of the composite may be measured after incubation in saline or other fluids. Repeated analysis will demonstrate whether degradation of the composite is linear or not, and mechanical testing of the incubated material will show the change in mechanical properties as the composite degrades. Such testing may also be used to compare the enzymatic and non-enzymatic degradation of the composite and to determine the levels of enzymatic degradation. A composite that is degraded is transformed into living bone upon implantation. A non-degradable composite leaves a supporting scaffold which may be interpenetrated with bone or other tissue.

Selection of Polymer

Practically any biocompatible polymer may be used in the composites of the invention. Biodegradable polymers may be preferable in some embodiments because composite made from such materials can be transformed into living bone. Polymers that do not degrade may be preferred for some applications, as they leave a supporting scaffold through which new living tissue may interpenetrate. Co-polymers and/or polymer blends may also be used in preparing the inventive composites. The selected polymer may be formable and settable under particular conditions, or a monomer or pre-polymer of the polymer may be used. In certain embodiments, the composite may become more formable when heated to or over a particular temperature, for example, a temperature at or above the glass transition temperature or melting point of the polymer component. Alternatively, the composite may be more formable when the polymer component has a certain cross-link density. After the mixture is injected or molded, the cross-link density of the polymer component of the composite may be increased to set the composite. In another embodiment, a small amount of monomer is mixed with the polymeric and bone components of the composite. Upon exposure to an energy source, e.g., UV light or heat, the monomer and polymer will further polymerize and/or cross-link, increasing the molecular weight, the cross-link density, or both. Alternatively or in addition, exposure to body heat, a chemical agent, or physiological fluids may stimulate polymerization.

If heat is employed to render the composite and/or the polymer component of the composite formable, the glass transition or melting temperature of the polymer component is preferably higher than normal body temperature, for example, higher than about 40° C. Polymers that become more formable at higher temperatures, e.g., higher than about 45° C., higher than about 50° C., higher than about 55° C., higher than about 60° C., higher than about 70° C., or higher than about 80° C., may also be used. However, the temperature required for rendering the composite formable should not so high as to cause unacceptable tissue necrosis upon implantation. Prior to implantation, the composite is typically sufficiently cooled to cause little or no tissue necrosis upon implantation. Exemplary polymers having $T_g$ suitable for use with the invention include but are not limited to starch-poly(caprolactone), poly(caprolactone), poly(lactide), poly(D,L-lactide), poly(lactide-co-glycolide), poly(D,L-lactide-co-glycolide), polycarbonates, polyurethane, tyrosine polycarbonate, tyrosine polyarylate, poly(orthoesters), polyphosphazenes, polypropylene fumarate, polyhydroxyvalerate, polyhydroxy butyrate, acrylates, methacrylates, and co-polymers, mixtures, enantiomers, and derivatives thereof. In certain particular embodiments, the polymer is starch-poly(caprolactone), poly(caprolactone), poly(lactide), poly(D,L-lactide), poly(lactide-co-glycolide), poly(D,L-lactide-co-glycolide), polyurethane, or a co-polymer, mixture, enantiomer, or derivative thereof. In certain embodiments, the polymer is poly(D,L-lactide). In certain other embodiments, the polymer is poly(D,L-lactide-co-glycolide). In certain embodiments, the polymer is poly(caprolactone). In certain embodiments, the polymer is a poly(urethane). In certain embodiments, the polymer is tyrosine polycarbonate. In certain embodiments, the polymer is tyrosine polyarylate.

It is not necessary for all such embodiments that the glass transition temperature of the polymer be higher than body temperature. In non-load bearing and some load-bearing applications, the viscosity of the polymer component and resulting composite need only be high enough at body temperature that the composite will not flow out of the implant site. In other embodiments, the polymer component may have crystalline and non-crystalline regions. Depending on the ratio of crystalline and non-crystalline material, a polymer may remain relatively rigid between the glass transition and melting temperatures. Indeed, for some polymers, the melting temperature will determine when the polymer material becomes formable.

Since the mixture may be rendered formable just prior to injection, polymer components with glass transition or melting temperatures higher than 80° C. are also suitable for use with the invention, despite the sensitivity of biological material to heat. For example, PMMA bone cement achieves temperatures of about 50-60° C. during curing. Potential damage to bone and/or other materials in the composite depends on both the temperature and the processing time. As the $T_g$ or $T_m$ of the polymer component increases, the composite should be heated for shorter periods of time to minimize damage to its biological components and should cool sufficiently quickly to minimize injury at the implantation site.

The $T_g$ of a polymer may be manipulated by adjusting its cross-link density and/or its molecular weight. Thus, for polymers whose glass transition temperatures are not sufficiently high, increasing the cross-link density or molecular weight can increase the $T_g$ to a level at which composites containing these polymers can be heated to render them formable. Alternatively, the polymer may be produced with crystalline domains, increasing the stiffness of the polymer at temperatures above its glass transition temperature. In addition, the $T_g$ of the polymer component may be modified by adjusting the percentage of the crystalline component. Increasing the volume fraction of the crystalline domains may so reduce the formability of the polymer between $T_g$ and $T_m$ that the composite has to be heated above its melting point to be sufficiently formable for use with the invention.

Where a monomer, prepolymer, or other partially polymerized or partially cross-linked polymer is employed in the inventive composite, the resulting polymer may form by step or chain polymerization. One skilled in the art will recognize that the rate of polymerization should be controlled so that any change in volume upon polymerization does not impact mechanical stresses on the included bone particles. The amount and kind of radical initiator, e.g., photo-active initiator (e.g., UV, infrared, or visible), thermally-active initiator, or chemical initiator, or the amount of heat or light employed, may be used to control the rate of reaction or modify the molecular weight. Where desired, a catalyst may be used to increase the rate of reaction or modify the molecular weight. For example, a strong acid may be used as a catalyst for step polymerization. Exemplary catalysts for ring opening polymerization include organotin compounds and glycols and other primary alcohols. Trifunctional and other multifunctional monomers or cross-linking agents may also be used to increase the cross-link density. For chain polymerizations, the concentration of a chemical initiator in the monomer-bone particle mixture may be adjusted to manipulate the final molecular weight.

Exemplary initiators are listed in George Odian's *Principles of Polymerization*, (3rd Edition, 1991, New York, John Wiley and Sons) and available from companies such as Polysciences, Wako Specialty Chemicals, Akzo Nobel, and Sigma. Polymerization initiators useful in the inventive composite include organic peroxides (e.g., benzoyl peroxide) and azo initiators (e.g., AIBN). Preferably, the initiator like the polymer and/or monomer is biocompatible. Alternatively, polymerized or partially polymerized material may be exposed to UV light, microwaves, or an electron beam to provide energy for inter-chain reactions. Polymerization may also be triggered by exposure to physiological temperatures or fluids. One skilled in the art will recognize how to modify the cross-link density to control the rate of degradation and the stiffness of the composite. For example, an accelerator such as an N,N-dialkyl aniline or an N,N-dialkyl toluidine may be used. Exemplary methods for controlling the rate of polymerization and the molecular weight of the product are also described in Odian (1991), the entire contents of which are incorporated herein by reference.

Any biocompatible polymer may be used to form composites for use with embodiments of the invention. As noted above, the cross-link density and molecular weight of the polymer may need to be manipulated so that the polymer can be formed and set when desired. In some embodiments, the formable polymer material may include monomers, low-molecular weight chains, oligomers, or telechelic chains of the polymers described herein, and these are cross-linked or further polymerized after implantation (e.g., injection). A number of biodegradable and non-biodegradable biocompatible polymers are known in the field of polymeric biomaterials, controlled drug release, and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; Beckamn et al., U.S. Patent Application 2005/0013793, published Jan. 20, 2005; see also Langer, *Acc. Chem. Res.* 33:94, 2000; Langer, *J. Control Release* 62:7, 1999; and Uhrich et al., *Chem. Rev.* 99:3181, 1999, the contents of all of which are incorporated herein by reference).

Other polymers useful in the present invention are described in U.S. patent applications, U.S. Ser. No. 10/735,135, filed on Dec. 12, 2003, entitled "Formable and settable polymer bone composite and method of production thereof" and published under No. 2005-0008672; U.S. Ser. No. 10/681,651, filed on Oct. 8, 2003, entitled "Coupling agents for orthopedic biomaterials" and published under No. 2005-0008620; and U.S. Ser. No. 60/760,538, filed on Jan. 19, 2006 and entitled "Injectable and Settable Bone Substitute Material", all of which are incorporated herein by reference.

In one embodiment, the polymer matrix is biodegradable. Exemplary biodegradable materials include lactide-glycolide copolymers of any ratio (e.g., 85:15, 40:60, 30:70, 25:75, or 20:80), poly(L-lactide-co-D,L-lactide), polyglyconate, poly(arylates), poly(anhydrides), poly(hydroxy acids), polyesters, poly(ortho esters), poly(alkylene oxides), polycarbonates, poly(propylene fumarates), poly(propylene glycol-co fumaric acid), poly(caprolactones), polyamides, polyesters, polyethers, polyureas, polyamines, polyamino acids, polyacetals, poly(orthoesters), poly(pyrolic acid), poly(glaxanone), poly(phosphazenes), poly(organophosphazene), polylactides, polyglycolides, poly(dioxanones), polyhydroxybutyrate, polyhydroxyvalyrate, polyhydroxybutyrate/valerate copolymers, poly(vinyl pyrrolidone), biodegradable polycyanoacrylates, biodegradable polyurethanes including glucose-based polyurethanes and lysine-based polyurethanes, and polysaccharides (e.g., chitin, starches, celluloses). In certain embodiments, the polymer used in the inventive composite is poly(lactide-co-glycolide). The ratio of lactide and glycolide units in the polymer may vary. Particularly useful ratios are approximately 45-80% lactide to approximately 44-20% glycolide. In certain embodiments, the ratio is approximately 50% lactide to approximately 50% glycolide. In other certain embodiments, the ratio is approximately 65% lactide to approximately 45% glycolide. In other certain embodiments, the ratio is approximately 60% lactide to approximately 40% glycolide. In other certain embodiments, the ratio is approximately 70% lactide to approximately 30% glycolide. In other certain embodiments, the ratio is approximately 75% lactide to approximately 25% glycolide. In certain embodiments, the ratio is approximately 80% lactide to approximately 20% glycolide. In certain of the above embodiments, lactide is D,L-lactide. In other embodiments, lactide is L-lactide. In certain particular embodiments, RESOMER® 824 (poly-L-lactide-co-glycolide) (Boehringer Ingelheim) is used as the polymer in the composite. In certain particular embodiments, RESOMER® 504 (poly-D,L-lactide-co-glycolide) (Boehringer Ingelheim) is used as the polymer in the composite. In certain particular embodiments, PURASORB PLG (75/25 poly-L-lactide-co-glycolide) (Purac Biochem) is used as the polymer in the composite. In certain particular embodiments, PURASORB PG (polyglycolide) (Purac Biochem) is used as the polymer in the composite. In certain embodiments, the polymer is PEGylated-poly(lactide-co-glycolide). In certain embodiments, the polymer is PEGylated-poly(lactide). In certain embodiments, the polymer is PEGylated-poly(glycolide). In other embodiments, the polymer is polyurethane. In other embodiments, the polymer is polycaprolactone. In certain embodiments, the polymer is a co polymer of poly(caprolactone) and poly(lactide). For polyesters such as poly (lactide) and poly(lactide-co-glycolide), the inherent viscosity of the polymer ranges from about 0.4 dL/g to about 5 dL/g. In certain embodiments, the inherent viscosity of the polymer ranges from about 0.6 dL/g to about 2 dL/g. In certain embodiments, the inherent viscosity of the polymer ranges from about 0.6 dL/g to about 3 dL/g. In certain embodiments, the inherent viscosity of the polymer ranges from about 1 dL/g to about 3 dL/g. In certain embodiments, the inherent viscosity of the polymer ranges from about 0.4 dL/g to about 1 dL/g. For poly(caprolactone), the inherent viscosity of the polymer ranges from about 0.5 dL/g to about 1.5 dL/g. In certain embodiments, the inherent viscosity of the poly(caprolactone) ranges from about 1.0 dL/g to about 1.5 dL/g. In certain embodiments, the inherent viscosity of the poly(caprolactone) ranges from about 1.0 dL/g to about 1.2 dL/g. In certain embodiments, the inherent viscosity of the poly(caprolactone) is about 1.08 dL/g. Natural polymers, including collagen, polysaccharides, agarose, glycosaminoglycans, alginate, chitin, and chitosan, may also be employed. Tyrosine-based polymers, including but not limited to polyarylates and polycarbonates, may also be employed (see Pulapura, et al., "Tyrosine-derived polycarbonates: Backbone-modified "pseudo"-poly(amino acids) designed for biomedical applications," *Biopolymers,* 1992, 32: 411-417; Hooper, et al., "Diphenolic monomers derived from the natural amino acid α-L-tyrosine: an evaluation of peptide coupling techniques," *J. Bioactive and Compatible Polymers,* 1995, 10:327-340, the contents of both of which are incorporated herein by reference). Monomers for tyrosine-based polymers may be prepared by reacting an L-tyrosine-derived diphenol compound with phosgene or a diacid (Hooper, 1995; Pulapura, 1992). Similar techniques may be used to prepare amino acid-based monomers of other amino acids having reactive side chains, including imines, amines, thiols, etc. The polymers described in the application entitled "Polyurethanes for Osteoimplants," filed on even date herewith, may also be used in embodiments of the present invention. In one embodiment, the degradation products include bioactive materials, biomolecules, small molecules, or other such materials that participate in metabolic processes.

Polymers may be manipulated to adjust their degradation rates. The degradation rates of polymers are well characterized in the literature (see *Handbook of Biodegradable Polymers,* Domb, et al., eds., Harwood Academic Publishers, 1997, the entire contents of which are incorporated herein by reference). In addition, increasing the cross-link density of a polymer tends to decrease its degradation rate. The cross-link density of a polymer may be manipulated during polymerization by adding a cross-linking agent or promoter. After polymerization, cross-linking may be increased by exposure to UV light or other radiation. Co-monomers or mixtures of polymers, for example, lactide and glycolide polymers, may be employed to manipulate both degradation rate and mechanical properties.

Non-biodegradable polymers may also be used as well. For example, polypyrrole, polyanilines, polythiophene, and derivatives thereof are useful electroactive polymers that can transmit voltage from endogenous bone to an implant. Other non-biodegradable, yet biocompatible polymers include polystyrene, polyesters, polyureas, poly(vinyl alcohol), polyamides, poly(tetrafluoroethylene), and expanded polytetrafluoroethylene (ePTFE), poly(ethylene vinyl acetate), polypropylene, polyacrylate, non-biodegradable polycyanoacrylates, non-biodegradable polyurethanes, mixtures and copolymers of poly(ethyl methacrylate) with tetrahydrofurfuryl methacrylate, polymethacrylate, poly(methyl methacrylate), polyethylene, including ultra high molecular weight polyethylene (UHMWPE), polypyrrole, polyanilines, polythiophene, poly(ethylene oxide), poly(ethylene oxide co-butylene terephthalate), poly ether-ether ketones (PEEK), and polyetherketoneketones (PEKK). Monomers that are used to produce any of these polymers are easily purchased from companies such as Polysciences, Sigma, and Scientific Polymer Products.

Those skilled in the art will recognize that this is an exemplary, not a comprehensive, list of polymers appropriate for in vivo applications. Co-polymers, mixtures, and adducts of the above polymers may also be used with the invention.

Additional Components

Additional materials may be included in the inventive composite. The additional material may be biologically active or inert. Additional materials may also be added to the composite to improve its chemical, mechanical, or biophysical properties. Additional materials may also be added to improve the handling or storage of the composite (e.g., a preservative). Those of skill in this art will appreciate the myriad of different components that may be included in the composite.

Additional components of the composite may be any type of chemical compound including proteins, peptides, polynucleotides (e.g., vectors, plasmids, cosmids, artificial chromosomes, etc.), lipids, carbohydrates, organic molecules, small molecules, organometallic compounds, metals, ceramics, polymers, etc. Living cells, tissue samples, or viruses may also be added to the inventive composites. In certain embodiments, the additional material comprises cells, which may optionally be genetically engineered. For example, the cells may be engineered to produce a specific growth factor, chemotactic factor, osteogenic factor, etc. In certain embodiments, the cells may be engineered to produce a polynucleotide such as an siRNA, shRNA, RNAi, microRNA, etc. The cell may include a plasmid, or other extra-chromosomal piece of DNA. In certain embodiments, a recombinant construct is integrated into the genome of the cell. In certain embodiments, the additional material comprises a virus. Again, the virus may be genetically engineered. Tissues such as bone marrow and bone samples may be combined with the composite of polymer and bone-derived particles. The composite may include additional calcium-based ceramics such as calcium phosphate and calcium carbonate. In certain embodiments, non-biologically active materials are incorporated into the composite. For example, labeling agents such as radiopaque, luminescent, or magnetically active particles may be attached to the bone-derived particles using silane chemistry or other coupling agents, for example zirconates and titanates, or mixed into the polymer, as described herein. Alternatively, or in addition, poly(ethylene glycol) (PEG) may be attached to the bone particles. Biologically active molecules, for example, small molecules, bioactive agents, and biomolecules such as lipids may be linked to the particles through silane SAMs or using a polysialic acid linker (see, for example, U.S. Pat. No. 5,846,951; incorporated herein by reference).

The composite may also include one or more other components such as a plasticizer. Plasticizer are typically compounds added to polymers or plastics to soften them or make them more pliable. Plasticizers soften, make workable, or otherwise improve the handling properties of a polymer or composite. Plasticizers also allow the inventive composite to be moldable at a lower temperature, thereby avoiding heat induced tissue necrosis during implantation. The plasticizer may evaporate or otherwise diffuse out of the composite over time, thereby allowing the composite to harden or set. Plasticizer are thought to work by embedding themselves between the chains of polymers. This forces the polymer chains apart and thus lowers the glass transition temperature of the polymer. Typically, the more plasticizer that is added, the more flexible the resulting polymer or composite will be.

In certain embodiments, the plasticizer is based on an ester of a polycarboxylic acid with linear or branched aliphatic alcohols of moderate chain length. For example, some plasticizers are adipate-based. Examples of adipate-based pasticizers include bis(2-ethylhexyl)adipate (DOA), dimethyl adipate (DMAD), monomethyl adipate (MMAD), and dioctyl adipate (DOA). Other plasticizers are based on maleates, sebacates, or citrates such as bibutyl maleate (DBM), diisobutylmaleate (DIBM), dibutyl sebacate (DBS), triethyl citrate (TEC), acetyl triethyl citrate (ATEC), tributyl citrate (TBC), acetyl tributyl citrate (ATBC), trioctyl citrate (TOC), acetyl trioctyl citrate (ATOC), trihexyl citrate (THC), acetyl trihexyl citrate (ATHC), butyryl trihexyl citrate (BTHC), and trimehtylcitrate (TMC). Other plasticizers are phthalate based. Examples of phthalate-based plasticizers are N-methyl phthalate, bis(2-ethylhexyl) phthalate (DEHP), diisononyl phthalate (DINP), bis(n-butyl) phthalate (DBP), butyl benzyl phthalate (BBzP), diisodecyl phthalate (DOP), diethyl phthalate (DEP), diisobutyl phthalate (DIBP), and di-n-hexyl phthalate. Other suitable plasticizers include liquid polyhydroxy compounds such as glycerol, polyethylene glycol (PEG), triethylene glycol, sorbitol, monacetin, diacetin, and mixtures thereof. Other plasticizers include trimellitates (e.g., trimethyl trimellitate (TMTM), tri-(2-ethylhexyl) trimellitate (TEHTM-MG), tri-(n-octyl,n-decyl) trimellitate (ATM), tri-(heptyl,nonyl) trimellitate (LTM), n-octyl trimellitate (OTM)), benzoates, epoxidized vegetable oils, sulfonamides (e.g., N-ethyl toluene sulfonamide (ETSA), N-(2-hydroxypropyl) benzene sulfonamide (HP BSA), N-(n-butyl) butyl sulfonamide (BBSA-NBBS)), organophosphates (e.g., tricresyl phosphate (TCP), tributyl phosphate (TBP)), glycols/polyethers (e.g., triethylene glycol dihexanoate, tetraethylene glycol diheptanoate), and polymeric plasticizers. Other plasticizers are described in *Handbook of Plasticizers* (G. Wypych, Ed., ChemTec Publishing, 2004), which is incorporated herein by reference. In certain embodiments, other polymers are added to the composite as plasticizers. In certain particular embodiments, polymers with the same chemical structure as those used in the composite are used but with lower molecular weights to soften the overall composite. In certain embodiments, oligomers or monomers of the polymers used in the composite are used as plasticizers. In other embodiments, different polymers with lower melting points and/or lower viscosities than those of the polymer component of the composite are used. In certain embodiments, oligomers or monomers of polymers different from those used in the composite are used as plasticizers. In certain embodiments, the polymer used as a plasticizer is poly(ethylene glycol) (PEG). The PEG used as a plasticizer is typically a low molecular weight PEG such as those having an average molecular weight of 1000 to 10000 g/mol, preferably from 4000 to 8000 g/mol. In certain embodiments, PEG 4000 is used in the composite. In certain embodiments, PEG 5000 is used in the composite. In certain embodiments, PEG 6000 is used in the composite. In certain embodiments, PEG 7000 is used in the composite. In certain embodiments, PEG 8000 is used in the composite. The plasticizer (PEG) is particularly useful in making more moldable composites that include poly(lactide), poly(D,L-lactide), poly(lactide-co-glycolide), poly(D,L-lactide-co-glycolide), or poly(caprolactone). In certain embodiments, PEG is grafted onto a polymer of the composite or is co-polymerized with a polymer of the composite.

Plasticizer may comprise 1-40% of the composite by weight. In certain embodiments, the plasticizer is 10-30% by weight. In certain embodiments, the plasticizer is approximately 10% by weight. In certain embodiments, the plasticizer is approximately 15% by weight. In certain embodiments, the plasticizer is approximately 20% by weight. In certain embodiments, the plasticizer is approximately 25% by weight. In certain embodiments, the plasticizer is approximately 30% by weight. In certain embodiments, the plasticizer is approximately 33% by weight. In certain embodiments, the plasticizer is approximately 40% by weight. In certain embodiments, a plasticizer is not used in the composite. For example, in some polycaprolactone-containing composites, a plasticizer is not used.

The inventive composite may be porous (e.g., at the time of manufacture), may be made porous prior to implantation, or may become porous upon implantation. For a general discussion of the use of porosity in osteoimplants, see U.S. patent application US 2005/0251267, published Nov. 10, 2005; which is incorporated herein by reference. A porous composite osteoimplant with an interconnecting network of pores has been shown to facilitate the invasion of cells and promote the organized growth of incoming cells and tissue (e.g., living bone). Allcock et al. "Synthesis of poly[(amino acid alkyl ester) phosphazenes" *Macromolecules* 10:824-830, 1977; Allcock et al. "Hydrolysis pathways for amino-phosphazenes" *Inorg. Chem.* 21:515-521, 1982; Mikos et al. "Prevascularization of biodegradable polymer scaffolds for hepatocyte transplantation" *Proc. ACS Div. of Polymer Mater.* 66:33, 1992; Eggli et al. "Porous hydroxyapatite and tricalcium phosphate cylinders with two different pore size ranges implanted in the cancellous bone of rabbits" *Clin. Orthop.* 232:127-138, 1987; each of which is incorporated herein by reference. Porosity has also been shown to influence the biocompatibility and bony integration of polymeric composites. White et al. "Biomaterial aspects of Interpore 200 porous hydroxyapatite" *Dental Clinical of N. Amer.* 30:49-67, 1986; which is incorporated herein by reference.

The porosity of the composite may include both open and closed cells. The terms "open cells" and "open-celled structure" are used herein interchangeably and refer to a porous material with very large permeability, and where no significant surface barriers exist between cells (i.e., where the pores are connected). The terms "closed cells" and "close-celled structure" are used herein interchangeably and refer to a porous material where the pores are not connected, resulting in a weakly permeable material. Open cells in an inventive composite increase the paths for tissue to infiltrate the composite and will decrease degradation times. The proportion and size distribution ranges of open and closed cells of the final inventive composite (e.g., before or after implantation) may be adjusted by controlling such factors as the identity of the porogen, percentage of porogen, percentage of particles, the properties of the polymer, etc.

The composites of the present invention can exhibit high degrees of porosity over a wide range of effective pore sizes. Thus, composites of the present invention may have, at once, macroporosity, mesoporosity and microporosity. Macroporosity is characterized by pore diameters greater than about 100 microns. Mesoporosity is characterized by pore diameters between about 100 microns about 10 microns; and microporosity occurs when pores have diameters below about 10 microns. In some embodiments, the composite has a porosity of at least about 30%. For example, in certain embodiments, the composite has a porosity of more than about 50%, more than about 60%, more than about 70%, more than bout 80%, or more than about 90%. Advantages of a highly porous composite over less porous or non-porous composite include, but are not limited to, more extensive cellular and tissue in-growth into the composite, more continuous supply of nutrients, more thorough infiltration of therapeutics, and enhanced revascularization, allowing bone growth and repair to take place more efficiently. Furthermore, in certain embodiments, the porosity of the composite may be used to load the composite with biologically active agents such as drugs, small molecules, cells, peptides, polynucleotides, growth factors, osteogenic factors, etc, for delivery at the implant site. Porosity may also render certain composites of the present invention compressible.

In certain particular embodiments, the pores of the composite are preferably over 100 microns wide for the invasion of cells and bony in-growth. Klaitwatter et al. "Application of porous ceramics for the attachment of load bering orthopedic applications" *J. Biomed. Mater. Res. Symp.* 2:161, 1971; each of which is incorporated herein by reference. In certain embodiments, the pore size ranges from approximately 50 microns to approximately 500 microns, preferably from approximately 100 microns to approximately 250 microns.

The porosity of the composite may be accomplished using any means known in the art. Exemplary methods of creating porosity in a composite include, but are not limited to, particular leaching processes, gas foaming processing, supercritical carbon dioxide processing, sintering, phase transformation, freeze-drying, cross-linking, molding, porogen melting, polymerization, melt-blowing, and salt fusion (Murphy et al. *Tissue Engineering* 8(1):43-52, 2002; incorporated herein by reference). For a review, see Karageorgiou et al., *Biomaterials* 26:5474-5491, 2005; incorporated herein by reference. The porosity may be a feature of the composite during manufacture or before implantation, or the porosity may only be available after implantation. For example, the implanted composite may include latent pores. These latent pores may arise from including porogens in the composite.

The porogen may be any chemical compound that will reserve a space within the composite while the composite is being molded and will diffuse, dissolve, and/or degrade prior to or after implantation leaving a pore in the composite. Porogens preferably have the property of not being appreciably changed in shape and/or size during the procedure to make the composite moldable. For example, the porogen should retain its shape during the heating of the composite to make it moldable. Therefore, the porogen preferably does not melt upon heating of the composite to make it moldable. In certain embodiments, the porogen has a melting point greater than about 60° C., greater than about 70° C., greater than about 80° C., greater than about 85° C., or greater than about 90° C.

Porogens may be of any shape or size. The porogen may be spheroidal, cuboidal, rectangular, elongated, tubular, fibrous, disc-shaped, platelet-shaped, polygonal, etc. In certain embodiments, the porogen is granular with a diameter ranging from approximately 100 microns to approximately 800 microns. In certain embodiments, the porogen is elongated, tubular, or fibrous. Such porogens provide increased connectivity of the pores of the composite and/or also allow for a lesser percentage of the porogen in the composite. The amount of the porogen may vary in the composite from 1% to 80% by weight. In certain embodiments, the plasticizer makes up from about 5% to about 80% by weight of the composite. In certain embodiments, the plasticizer makes up from about 10% to about 50% by weight of the composite. Pores in the composite are thought to improve the osteoinductivity or osteoconductivity of the composite by providing holes for cells such as osteoblasts, osteoclasts, fibroblasts, cells of the osteoblast lineage, stem cells, etc. The pores provide the composite with biological in growth capacity. Pores in the composite may also provide for easier degradation of the composite as bone is formed and/or remodeled. Preferably, the porogen is biocompatible.

The porogen may be a gas, liquid, or solid. Exemplary gases that may act as porogens include carbon dioxide, nitrogen, argon, or air. Exemplary liquids include water, organic solvents, or biological fluids (e.g., blood, lymph, plasma). The gaseous or liquid porogen may diffuse out of the osteoimplant before or after implantation thereby providing pores for biological in-growth. Solid porogens may be crystalline or amorphous. Examples of possible solid porogens include water soluble compounds. In certain embodiments, the water soluble compound has a solubility of greater than 10 g per 100 mL water at 25° C. In certain embodiments, the water soluble compound has a solubility of greater than 25 g per 100 mL water at 25° C. In certain embodiments, the water soluble compound has a solubility of greater than 50 g per 100 mL water at 25° C. In certain embodiments, the water soluble compound has a solubility of greater than 75 g per 100 mL water at 25° C. In certain embodiments, the water soluble compound has a solubility of greater than 100 g per 100 mL water at 25° C. Examples of porogens include carbohydrates (e.g., sorbitol, dextran (poly(dextrose)), starch), salts, sugar alcohols, natural polymers, synthetic polymers, and small molecules.

In certain embodiments, carbohydrates are used as porogens in the inventive composites. The carbohydrate may be a monosaccharide, disaccharide, or polysaccharide. The carbohydrate may be a natural or synthetic carbohydrate. Preferably, the carbohydrate is a biocompatible, biodegradable carbohydrate. In certain embodiments, the carbohydrate is a polysaccharide. Exemplary polysaccharides include cellulose, starch, amylose, dextran, poly(dextrose), glycogen, etc. In certain embodiments, the polysaccharide is dextran. Very high molecular weight dextran has been found particularly useful as a porogen. For example, the molecular weight of the dextran may range from about 500,000 g/mol to about 10,000,000 g/mol, preferably from about 1,000,000 g/mol to about 3,000,000 g/mol. In certain embodiments, the dextran has a molecular weight of approximately 2,000,000 g/mol. Dextrans with a molecular weight higher than 10,000,000 g/mol may also be used as porogens. Dextran may be used in any form (e.g., particles, granules, fibers, elongated fibers) as a porogen. In certain embodiments, fibers or elongated fibers of dextran are used as the porogen in the inventive composite. Fibers of dextran may be formed using any known method including extrusion and precipitation. Fibers may be prepared by precipitation by adding an aqueous solution of dextran (e.g., 5-25% dextran) to a less polar solvent such as a 90-100% alcohol (e.g., ethanol) solution. The dextran precipitates out in fibers that are particularly useful as porogens in the inventive composite. Dextran may be about 15% by weight to about 30% by weight of the composite. In certain embodiments, dextran is about 15% by weight, 20% by weight, 25% by weight, or 30% by weight. Higher and lower percentages of dextran may also be used. Once the composite with the dextran as a porogen is implanted into a subject, the dextran dissolves away very quickly. Within approximately 24 hours, substantially all of the dextran is out of the composite leaving behind pores in the osteoimplant composite. An advantage of using dextran in the composite is that dextran exhibits a hemostatic property in the extravascular space. Therefore, dextran in a composite can decrease bleeding at or near the site of implantation.

Small molecules including pharmaceutical agents may also be used as porogens in the inventive composites. Examples of polymers that may be used as plasticizers include poly(vinyl pyrollidone), pullulan, poly(glycolide), poly(lactide), and poly(lactide-co-glycolide). Typically low molecular weight polymers are used as porogens. In certain embodiments, the porogen is poly(vinyl pyrrolidone) or a derivative thereof. Plasticizers that are removed faster than the surrounding composite can also be considered porogens.

In certain embodiments, the composite may include a wetting or lubricating agent. Suitable wetting agents include water, organic protic solvents, organic non-protic solvents, aqueous solutions such as physiological saline, concentrated saline solutions, sugar solutions, ionic solutions of any kind, and liquid polyhydroxy compounds such as glycerol, polyethylene glycol (PEG), polyvinyl alcohol (PVA), and glycerol esters, and mixtures of any of these. Biological fluids may also be used as wetting or lubricating agents. Examples of biological fluids that may be used with the inventive composites include blood, lymph, plasma, serum, or marrow. Lubricating agents may include, for example, polyethylene glycol, which can be combined with the polymer and other components to reduce viscosity or even coated on the walls of the delivery device. Alternatively or in addition, the particulate material may be coated with a polymer by sputtering or other techniques known to those skilled in the art.

Additionally, composites of the present invention may contain one or more biologically active molecules, including biomolecules, small molecules, and bioactive agents, to promote bone growth and connective tissue regeneration, and/or to accelerate healing. Examples of materials that can be incorporated include chemotactic factors, angiogenic factors, bone cell inducers and stimulators, including the general class of cytokines such as the TGF-β superfamily of bone growth factors, the family of bone morphogenic proteins, osteoinductors, and/or bone marrow or bone forming precursor cells, isolated using standard techniques. Sources and amounts of such materials that can be included are known to those skilled in the art.

In certain embodiments, the composite include antibiotics. The antibiotics may be bacteriocidial or bacteriostatic. Other anti-microbial agents may also be included in the composite. For example, anti-viral agents, anti-protazoal agents, anti-parasitic agents, etc. may be include in the composite. Other suitable biostatic/biocidal agents include antibiotics, povidone, sugars, and mixtures thereof.

Biologically active materials, including biomolecules, small molecules, and bioactive agents may also be combined with the polymer and particles to, for example, stimulate particular metabolic functions, recruit cells, or reduce inflammation. For example, nucleic acid vectors, including plasmids and viral vectors, that will be introduced into the patient's cells and cause the production of growth factors such as bone morphogenetic proteins may be included in the composite. Biologically active agents include, but are not limited to, antiviral agent, antimicrobial agent, antibiotic agent, amino acid, peptide, protein, glycoprotein, lipoprotein, antibody, steroidal compound, antibiotic, antimycotic, cytokine, vitamin, carbohydrate, lipid, extracellular matrix, extracellular matrix component, chemotherapeutic agent, cytotoxic agent, growth factor, anti-rejection agent, analgesic, anti-inflammatory agent, viral vector, protein synthesis co-factor, hormone, endocrine tissue, synthesizer, enzyme, polymer-cell scaffolding agent with parenchymal cells, angiogenic drug, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite, and penetraction enhancer. Additional exemplary substances include chemotactic factors, angiogenic factors, analgesics, antibiotics, anti-inflammatory agents, bone morphogenic proteins, and other growth factors that promote cell-directed degradation or remodeling of the polymer phase of the composite and/or development of new tissue (e.g., bone). RNAi or other technologies may also be used to reduce the production of various factors.

To enhance biodegradation in vivo, the composites of the present invention can also include different enzymes. Examples of suitable enzymes or similar reagents are proteases or hydrolases with ester-hydrolyzing capabilities. Such enzymes include, but are not limited to, proteinase K, bromelaine, pronase E, cellulase, dextranase, elastase, plasmin streptokinase, trypsin, chymotrypsin, papain, chymopapain, collagenase, subtilisin, chlostridopeptidase A, ficin, carboxypeptidase A, pectinase, pectinesterase, an oxireductase, an oxidase, or the like. The inclusion of an appropriate amount of such a degradation enhancing agent can be used to regulate implant duration.

These materials need not be covalently bonded to a component of the composite. A material may be selectively distributed on or near the surface of the composite using the layering techniques described above. While the surface of the composite will be mixed somewhat as the composite is manipulated in the implant site, the thickness of the surface layer will ensure that at least a portion of the surface layer of the composite remains at the surface of the implant. Alternatively or in addition, biologically active components may be covalently linked to the bone particles before combination with the polymer. For example, silane coupling agents having amine, carboxyl, hydroxyl, or mercapto groups may be attached to the bone particles through the silane and then to reactive groups on a biomolecule, small molecule, or bioactive agent.

The composite may also be seeded with cells. In certain embodiments, a patient's own cells are obtained and used in the inventive composite. Certain types of cells (e.g., osteoblasts, fibroblasts, stem cells, cells of the osteoblast lineage, etc.) may be selected for use in the composite. The cells may be harvested from marrow, blood, fat, bone, muscle, connective tissue, skin, or other tissues or organs. In certain embodiments, a patient's own cells may be harvested, optionally selected, expanded, and used in the inventive composite. In other embodiments, a patient's cells may be harvested, selected without expansion, and used in the inventive composite. Alternatively, exogenous cells may be employed. Exemplary cells for use with the invention include mesenchymal stem cells and connective tissue cells, including osteoblasts, osteoclasts, fibroblasts, preosteoblasts, and partially differentiated cells of the osteoblast lineage. The cells may be genetically engineered. For example, the cells may be engineered to produce a bone morphogenic protein.

In embodiments where the polymer component becomes formable when heated, the heat absorbed by particles in the composite may increase the cooling time of the composite, extending the time available to form the composite into an implant. Depending on the relative heat capacities of the particle and the polymer components and the size of the particles, the particles may continue to release heat into the surrounding polymer after the time when the polymer alone would have cooled. The size and density distribution of particles within the composite may be optimized to adjust the amount of heat released into portions of an osteoimplant during and after implantation.

Administration of the Composite Material

The inventive composite may be administered to a subject in need thereof using any technique known in the art. The subject is typically a patient with a disorder or disease related to bone. In certain embodiments, the subject has a bony defect such as a fracture. The subject is typically a mammal although any animal with bones may benefit from treatment with the inventive composite. In certain embodiments, the subject is a vertebrate (e.g., mammals, reptiles, fish, birds, etc.). In certain embodiments, the subject is a human. In other embodiments, the subject is a domesticated animal such as a dog, cat, horse, etc. Any bone disease or disorder may be treated using the inventive composite including genetic diseases, congenital abnormalities, fractures, iatrogenic defects, bone cancer, bone metastases, inflammatory diseases (e.g. rheumatoid arthritis), autoimmune diseases, metabolic diseases, and degenerative bone disease (e.g., osteoarthritis). In certain embodiments, the inventive osteoimplant composites are formulated for the repair of a simple fracture, compound fracture, or non-union; as an external fixation device or internal fixation device; for joint reconstruction, arthrodesis, arthroplasty, or cup arthroplasty of the hip; for femoral or humeral head replacement; for femoral head surface replacement or total joint replacement; for repair of the vertebral column, spinal fusion or internal vertebral fixation; for tumor surgery; for deficit filling; for discectomy; for laminectomy; for excision of spinal tumors; for an anterior cervical or thoracic operation; for the repairs of a spinal injury; for scoliosis, for lordosis or kyphosis treatment; for intermaxillary fixation of a fracture; for mentoplasty; for temporomandibular joint replacement; for alveolar ridge augmentation and reconstruction; as an inlay osteoimplant; for implant placement and revision; for sinus lift; for a cosmetic procedure; for revision surgery; for revision surgery of a total joint arthroplasty; and for the repair or replacement of the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones. In certain embodiments, the inventive composite is used to seal a defect, void, or hole in a bone. For example, a bony defect may be filled with mineralized and/or partially or fully demineralized allograft bone or other bone substitute material, and the defect is sealed with the inventive composite.

The composite material is typically administered to a patient in a clinical setting. In certain embodiments, the osteoimplant composite is administered during a surgical procedure. The osteoimplant composite may be placed at an implant site by molding, placing, injecting, or extruding the inventive composite into the site of implantation. The composite is typically made moldable or flowable before it is administered to a subject. This allows the composite to fit into irregularly shaped sites. In certain embodiments, the composite of the particles with the polymer is injected or extruded into a tissue site (e.g., a bony defect). In one embodiment, the mixture is injected using minimally invasive surgical techniques or through a transcutaneous procedure such as percutaneous vertebroplasty. The procedure may not require a surgical incision or opening of the patient as required for traditional surgical procedures. For example, the mixture may be injected using a needle and syringe. The syringe may be driven by hand or mechanically. The needle may be positioned by radiological means before injection of the composite. It may be desirable to include a rigid injection system to provide more precise control over the injected volume.

The technique employed to deliver the flowable composite depends in part on the flow rate F of the material through the delivery device, which in turn depends in part on the resistance to flow of the composite. For laminar flow, the resistance to flow R is defined by the Poisseule equation, $$R = \frac{8\eta L}{\pi r^4} \qquad (1)$$

where $\eta$ is the viscosity, L is the length of the flow, and r is the radius of the bore through which the material is flowing. Thus, for injection through a long needle or deep into a tissue, a larger bore cannula may be useful to reduce flow resistance. Back pressure from the injection site may also dictate the desired cannula size or delivery device, since the flow rate depends on the back pressure as $$F = \frac{P_1 - P_2}{R} \qquad (2)$$

where $P_1$ and $P_2$ are the inlet and outlet pressures of the cannula.

One skilled in the art will recognize that one of the factors influencing the length of the flow is the distance from the injection site to the access point for the extruder or needle. In some embodiments, the mixture is injected percutaneously. A bony injection site may be some distance from the skin, necessitating a longer needle. In other embodiments, the injection site may be exposed, for example, during surgery. In these cases a very short cannula may suffice for delivery of the mixture, and a wider bore cannula may be appropriate.

One skilled in the art will recognize that a variety of cannula sizes may be employed to deliver mixtures according to embodiments of the invention. For example, a wider gauge may be desired for longer cannulae. Depending on the factors below, cannulae of 6 gauge or narrower, for example, 7 gauge, 8 gauge, 9 gauge, 10 gauge, 11 gauge, or 12 gauge, may be employed for percutaneous injection. In certain particular embodiments, a cannulae of 10 gauge, 11 gauge, or 12 gauge is used. Where the injection site is exposed or the injection is made using minimally invasive surgical techniques, even wider cannulae, e.g., 5 gauge, 3 gauge, about 1 cm, or wider. The optimal wall thickness may be easily tested by testing the yield strength of the needles under pressure. The taper on needles and cannulae may be optimized for the tissue or material that needs to be penetrated, independently of the characteristics of the composite being delivered.

The flow characteristics of the composite are also influenced by the ratio of the carrier to the solid particles and the interaction of the particles with the carrier and with each other. As the composite is injected, a "filter cake" may form at the entrance to the cannula; likewise, porous tissue at the implant site may also act as a filter, allowing the carrier to flow more easily than the particles and promoting the formation of a filter cake. Filtering may be alleviated by increasing the difference between the actual carrier/particle ratio and the plastic limit. The plastic limit may be decreased by using more regularly shaped particles instead of elongated particles, by increasing the breadth of the particle size distribution, by reducing agglomeration of the dry particles before blending with the carrier, and by reducing the degree of interparticle interactions, for example by changing the surface charge or by adsorbing a polymer onto the surface of the particles. The thickness of the filter cake is directly proportional to the particle size, proportional to the square root of the cannula length, and inversely proportional to the square of the internal diameter of the cannula. Decreasing the delivery rate may also reduce filtering.

Another factor influencing the delivery is the potential degree of extravasation, the "leaking" of the mixture into the marrow space or outside the bone tissue, e.g., when the composite is injected into bone tissue. Extravasation may be reduced by increasing the viscosity of the composite. In many cases, extravasation may be prevented or reduced if the pressure required for extravasation is greater than that required to inject the coposite into the desired site, which need not be the same as $P_2$. However, as the porosity and the pore size at the injection site decrease, the pressure required to infiltrate the tissue increases.

In other embodiments, the composite is molded into a shape that can be placed into a tissue site. After placement, the composite may be further manipulated to better fit the site. Optionally, the composite is then caused to be set. The composite may be set by the addition of an agent such as a chemical agent, addition of energy such as UV light, or addition of heat. In some embodiments, the composite is set by allowing the implanted composite to cool to body temperature or by allowing a solvent or plasticizer to diffuse out from the composite.

The size of the particles may also dictate the delivery technique. The device used to deliver the composite should have a sufficient diameter that the particles do not clog the device. The particles may also be treated to reduce clogging, for example, by smoothing their surfaces, coating the particles, surface treating to improve their lubricity, or simply reducing their size.

All of these factors may be easily optimized for a particular injection site. Theoretical discussions of the factors described above are found in Bohner, et al., *Biomaterials*, (2003) 24:2721-2730, and Bohner, et al., (2005) 26:1553-1563, the contents of both of which are incorporated herein by reference. The characteristics of various types of injection sites (e.g., osteoporotic tissue, cancellous bone, cortical bone, substantially bone-free wound sites within bone) may be modeled with open cell aluminum foam blocks (see Giannitsios, et al., *European Cells and Materials*, Vol 10 Suppl 3 (2005), p. 54, the entire contents of which are incorporated herein by reference). Such blocks may be reproducibly produced and thus are suitable for modeling various types of bony tissue. For example, blocks may be produced with various pore sizes and porosities and injected, e.g., first with polymers of different viscosities to identify an optimal viscosity range, and then with polymer mixtures within the viscosity range but having different volume fractions of particles. Alternatively or in addition, the porous blocks may also be produced to duplicate an individual patient's wound site, which can be characterized using x-ray, MRI, and other imaging techniques.

In some embodiments, the composite is heated above the glass transition temperature of the polymer component in preparation for injection or extrusion. As discussed above, where the glass transition temperature is greater than body temperature, it should not be heated to temperature so great that either the tissue site or biological material in the composite is damaged. If the composite does not need to be held at an elevated temperature for a long period of time, a higher temperature may be used without damaging biological materials.

As discussed herein, in some embodiments, the mixture includes a monomer, prepolymer, or telechelic polymer that is polymerized in situ. An initiator or catalyst may be injected into the tissue site as part of the composite or after the composite is injected. Alternatively or in addition, the mixture is exposed to conditions that stimulate polymerization after injection. In another embodiment, a lower molecular weight polymer is used in the composite and then cross-linked and/or further polymerized following implantation. Of course, if a polymer is sufficiently viscous at body temperature, even if that is greater than the glass transition temperature, no pre- or post-injection processing of the mixture may be necessary.

After implantation, the composite typically stays at the site of implantation and is gradually resorbed by the body as bone forms in and around it. The composite is typically engineered to provide the mechanical strength necessary for the implantation site. The composite may be resorbed after approximately 1 month to approximately 6 years. The resorption rate will depend on the polymer used in the composite, the site of implantation, the patient, disease condition, etc. In certain embodiments, the composite lasts from approximately 1 month to approximately 6 months. In other embodiments, the composite lasts from approximately 6 months to approximately 1 year. In other embodiments, the composite lasts from approximately 1-2 years. In other embodiments, the composite lasts from approximately 2-3 years. In other embodiments, the composite lasts from approximately 5 years.

These and other aspects of the present invention will be further appreciated upon consideration of the following Examples, which are intended to illustrate certain particular embodiments of the invention but are not intended to limit its scope, as defined by the claims.

EXAMPLES

Example 1—50:50 Bone Particles and Polycaprolactone

A 50:50 mixture (by weight) of bovine bone fibers averaging 1-2 mm in length and polycaprolactone was placed into a test tube. The composite was heated in a plastic syringe in a microwave oven until the temperature exceeded 60° C. The syringe was placed in a hand-driven press and the composite injected out. A similar composite was prepared with 200-500 micron particles and exhibited improved extrusion characteristics.

A 50:50 mixture (by weight) of bovine bone fiber (300-800 microns sieved) and polycaprolactone were mixed into a uniform composite by heating the polymer in a microwave until melted. The composite was then mixed by hand and the heating and melting repeated until the mixture was uniform. A 65:35 mixture was formed in the same manner. A 50:50 mixture of polycaprolactone and bone fibers, with 10% polyethylene glycol (PEG) (10,000 Da) was produced by first melting the PEG and then adding the bone particles. The polycaprolactone was then melted and the composite hand-mixed until uniform.

The 50:50/PEG composite was heated between two platens until moldable and fit into a cylindrical housing having a 3.3 mm ID×5 cm cannula on one end and a piston on the other. The assembled housing was submerged in a 70° C. water bath for about 10 minutes. The composite was forced out of the cannula by driving the piston. The composite extruded at a uniform rate from the cannula at about 0.5 cm/s. About 5 cm³ of the composite was extruded.

The composite was injected into a cortical defect. The composite molded itself to the shape of the defect. Once the composite cooled (about 1 minute), a rigid composite plug remained in the defect.

Example 2—Sawbone Trial

A composite of 60/40 (bovine bone fiber/polycaprolactone (PCL)) was heated to approximately 65° C. and packed into SAWBONES™ defects of the following approximate shapes and sizes:
1. 3 cm diameter×1 cm depth defect.
2. A small defect 1 cm diameter×1 cm depth.
3. Lined the entire acetabular inner surface with polymer thinly spread over the inner surface.
4. Many other Sawbones defects of various sizes.

Upon cooling and setting, the composite was either very difficult to remove or could not be removed from the defect by hand for all the above cases.

For some of the above defects (#1 and #3), pilot holes were drilled and metal screws with different thread profiles were placed into the PCL composite. The screws cut their own threads into the material. The PCL composite (when warm and moldable) was also placed around the threads of various metal screws with different thread profiles. In both the tapped and moldable cases, using the protruding part of the screw as a "handle", the composite/screw combination could not be removed from the defect, and the screw could not be pulled from the PCL composite by hand.

Example 3—Excised Rabbit Femur Cylindrical Defect Trials

In another example, a 4.8 mm drill bit was used to create an approximately 10 mm long defect in the distal part of a wet, excised rabbit femur at room temperature. The defect was packed in one femur by heating 80/20 PCL/bovine bone particles to approximately 65° C., forming the composite by hand into the rough shape of a cylinder with a diameter smaller than the defect, and then placing the cylinder in the defect, followed by immediately tamping the material into the defect to fill it. Excess material on the outside of the defect was removed (sheared off by hand) before the composite cooled. Upon cooling, the composite could not be pulled out of the wet defect by hand.

In another case, using the same defect as described above (i.e., an approximately 10 mm long defect in the distal part of a wet, excised rabbit femur at room temperature), a composite of 50/50 PCL/bovine bone particles was heated to approximately 65° C. and small portions of the composite were pinched off and packed into the defect with the aid of a small cylindrical tamp. Approximately three small pieces of the warm composite were packed into the defect, one on top of the other, until the defect was filled. Upon cooling, the composite could not be pulled out of the wet defect by hand.

Water could be used to induce the composite to set more quickly. Irrigation with room temperature saline may achieve the same effect. The moldable composite interdigitated in the crevices of the individual host trabeculae thereby anchoring the implant when it cooled to a rigid form.

Example 4—Moldable Bone/Polymer Composite

Three composites of bone fibers and poly(caprolactone) (PCL) were prepared using the following percentages of bone fibers and polymer.

| % Bone Fibers | % PCL |
|---|---|
| 50 | 50 |
| 65 | 35 |
| 80 | 20 |

The percentages are by weight. A total of 1 g of each composite was prepared.

The appropriate amount of poly(caprolactone) (inherent viscosity of 1.08 dl/g) was weighed out and heated to approximately 100° C. for approximately 5-10 minutes until the polymer softened. The appropriate amount of rabbit bone fibers, which had been sieved to between 0.85 mm and 0.30 mm, was then added to the melted polymer and mixed into the polymer until the mixture was substantially homogenous. The composite was then cooled to room temperature and packaged in sterile bags and sealed in foil pouches before sterilization by terminal gamma irradiation. Five samples of each of the three composites were prepared.

The composites were graded according to how the heated composite feels to the touch and how well it conforms when packing a small void. Each composite was given a grade on a scale from 1 to 5 (1=poor handling, 5=optimal handling). The grades represent the following handling of the composite.

Grade 1—Material is brittle and crumbly; material does not hold together well (i.e., falls apart when handled); lack of cohesiveness between bone and polymer is extremely noticeable.

Grade 2—Material holds together somewhat but may be overly wet or sticky (e.g., sticks to the handler's gloves rather than defect); material takes a long time to set up or to soften; material often migrates from the defect site; and/or the material hardens to rapidly to manipulate into a defect site (e.g., sets up in less than 1 minute, less than 1 minute of working time).

Grade 3—Material is cohesive and pliable for at least 1-2 minutes of working time; material may stick lightly to the handler's gloves but is easily removed; and/or material stays in the defect site with little trouble or packs in easily.

Grade 4—Material is cohesive and pliable and has a working time of 2-4 minutes; material does not stick to the handler's gloves; and/or material is easily packing into a defect site.

Grade 5—Material is cohesive and pliable for 4-6 minutes; material does not stick to the handler's gloves and is easily packed into a defect site.

The 50/50 bone/polymer composite was extremely easy to work with. The composite could be manipulated for several minutes before setting up. On a scale of 1 to 5 (5 being the best), this composite was rated a 4 for handling and moldability.

The 65/35 bone/polymer composite was more difficult to prepare due to the greater quantity of bone fibers that had to be worked into the polymer. Handling of this composite was somewhat more difficult, and the composite setup more quickly. Handling for this composite was rated a 3.

The 8020 bone/polymer composite was even more difficult to prepare. The samples were crumbly with bone fibers falling out of the polymer. Handling for this composite was rated a 1.

Various mechanical properties of bone fiber/poly(caprolactone) (PCL) composites (70/30 bone/polymer and 50/50 bone/polymer) are given in the table below entitled "Mechanical Testing Summary".

| | | | Fatigue | | | |
|---|---|---|---|---|---|---|
| | | Compression | 25 MPa | Resid. | | |
| Polymer | Sample (ratio) | N | Yield Stress (Mpa) | N | (million cycles) | Yld. Str. (Mpa) | Hydration | Molding Method |

Mechanical Testing Summary

| Polymer | Sample (ratio) | N | Yield Stress (Mpa) | N | Fatigue 25 MPa (million cycles) | Resid. Yld. Str. (Mpa) | Hydration | Molding Method |
|---|---|---|---|---|---|---|---|---|
| PCL | Fibers (70/30) | 10 | 21.5 + 0.7 | 4 | 1.11 + 0.1** | 22.99 | 14 day | Comp. M. |
| PCL | Fibers (50/50) | 2 | 25.6 + 0.0 | | | | 1 day | Hand Mold |

**= some samples failed

Example 5—Moldable Bone/Polymer Composite

The following exemplary bone/polymer composites were prepared and tested for their mechanical properties after hydration. The composites were also rated on a scale of 1 to 5 (5 being the best) for their molding and handling properties. The grading scale for the handling is described above in Example 4. The molding rating is simply the number of cycles required on a microwave set at the "popcorn" setting to make it moldable. Lower numbers are typically more desirable than higher numbers.

| Composite | Molding Rating | Handling Rating | Hydration Incubation Time (hrs.) | Average Compressive Strength (MPa) | Average Modulus (MPa) | Compressive Strength (MPa) | Modulus (MPa) |
|---|---|---|---|---|---|---|---|
| 80% poly-L-lactide-co-glycolide (82:18) (Resomer 824) 20% PEG | 5 | 1 | 24 | 33.93 | 426.78 | 32.14 35.72 | 362.35 968.73 |
| 37.5% poly-L-lactide-co-D,L-lactide (70:30) (Resomer LR706) 30% PEG-8000 37.5% Bone fibers | 1.5 | 2.5 | 168 | 3.38 | 89.96 | 3.42 3.33 | 87.04 92.88 |
| 40% poly-L-lactide-co-glycolide (75:25) (Purac) 30% PEG-8000 30% Bone fibers | 1.5 | 2.5 | 188 | 7.82 | 113.245 | 5.26 10.38 | 24.35 202.14 |
| 38% PEGylated-poly-D,L-lactide (Lakeshore) 24% PEG-8000 38% Bone fibers | 1.5 | 3.5 | 168 | 21.645 | 357.35 | 21.05 22.24 | 386.45 328.25 |
| 50% poly-D,L-lactide-co-caprolactone (96/4) 10% PEG-8000 40% Bone fibers | 1.5 | 4 | 168 | | | | |
| 50% poly-D,L-lactide-co-caprolactone (96/4) 20% PEG-8000 30% Bone fibers | 0.75 | 4.5 | 24 | 30.76 | 1209.76 | | |
| 50% PEGylated poly-D,L-lactide (Lakeshore) 10% PEG-8000 40% Bone fibers | 1 | 2 | | | | | |
| 50% poly-L-lactide-co-glycolide (75:25) (Purac) 30% PEG-8000 20% Bone fibers | 1 | 3.5 | 24 | 30.39 | 672.64 | | |
| 46.7% poly-D,L-lactide-co-glycolide 20% PEG 33% Bone fibers | 3 | 4 | 24 | 41.2 | 1406.3 | 41.2 | 1406.3 |
| 50% poly-D,L-lactide-co-glycolide 10% PEG 40% Bone fibers | 2 | 3 | 24 | 60.39 | 1814.94 | 60.39 | 1814.94 |
| 40% poly-D,L-lactide-co-glycolide 20% PEG 40% Bone fibers | 1 | 4 | 24 | 46.54 | 1635.01 | 46.54 | 1635.01 |
| 40% poly-D,L-lactide-co-glycolide 10% PEG 50% Bone fibers | 1.5 | 3.5 | 24 | 65.05 | 1886.65 | 65.05 | 1886.65 |
| 60% poly-D,L-lactide-co-glycolide 20% PEG 20% Bone fibers | 1 | 4 | 24 | 47.79 | 1502.37 | 47.79 | 1502.37 |
| 40% poly-D,L-lactide-co-glycolide 40% PEG 20% Bone fibers | 1 | 4 | 24 | 11.04 | 222.9 | 11.04 | 222.9 |
| 50% poly-D,L-lactide-co-glycolide 10% PEG 40% Bone fibers | 1.5 | 3 | 24 | 38.89 | 733.975 | 38.89 | 733.975 |

-continued

| Composite | Molding Rating | Handling Rating | Hydration Incubation Time (hrs.) | Average Compressive Strength (MPa) | Average Modulus (MPa) | Compressive Strength (MPa) | Modulus (MPa) |
|---|---|---|---|---|---|---|---|
| 40% poly-D,L-lactide-co-glycolide 20% PEG 40% Bone fibers | 1 | 4 | 24 | 27.64 | 666.125 | 27.64 | 666.125 |

EQUIVALENTS AND SCOPE

The foregoing has been a description of certain non-limiting preferred embodiments of the invention. Those skilled in the art will recognize, or be able to ascertain using no more than routine experimentation, many equivalents to the specific embodiments of the invention described herein. Those of ordinary skill in the art will appreciate that various changes and modifications to this description may be made without departing from the spirit or scope of the present invention, as defined in the following claims.

In the claims articles such as "a", "an", and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects is excluded are not set forth explicitly herein.

What is claimed is:

1. A composite osteoimplant comprising: a plurality of particles comprising an inorganic material, a bone substitute material, a bone-derived material, or any combination thereof; and a polymer with which the plurality of particles has been combined; wherein the composite is moldable or flowable; and wherein the composite becomes set upon exposure to suitable conditions for setting the composite, wherein the suitable conditions for setting the composite include cooling the composite to a temperature below approximately 60° C.

2. The composite osteoimplant of claim 1, wherein the polymer has penetrated the pores, spaces, or voids of the particles.

3. The composite osteoimplant of claim 1, wherein the composite is moldable.

4. The composite osteoimplant of claim 1, wherein the composite can be shaped manually.

5. The composite osteoimplant of claim 1, wherein the composite can be shaped using a surgical instrument.

6. The composite osteoimplant of claim 1, wherein the composite can be shaped using a machine.

7. The composite osteoimplant of claim 1, wherein the composite is injectable.

8. The composite osteoimplant of claim 7, whereby the composite is suitable for injection through a 3 gauge or narrower needle.

9. The composite osteoimplant of claim 7, whereby the composite is suitable for injection through a 5 gauge or narrower needle.

10. The composite osteoimplant of claim 7, whereby the composite is suitable for injection through a 7 gauge or narrower needle.

11. The composite osteoimplant of claim 7, whereby the composite is suitable for injection through a 10 gauge or narrower needle.

12. The composite osteoimplant of claim 7, whereby the composite is suitable for injection through a 12 gauge or narrower needle.

13. The composite osteoimplant of claim 1, wherein the suitable conditions for setting the composite include changing the temperature of the composite, changing the osmotic pressure of the composite, exposing the composite to electromagnetic radiation, cross-linking the composite, exposing the composite to a chemical agent, changing the water or solvent content of the composite, changing the content of a component of the composite, or changing a diffusion gradient.

14. The composite osteoimplant of claim 1, wherein the suitable conditions for setting the composite include cooling the composite.

15. The composite osteoimplant of claim 1, wherein the suitable conditions for setting the composite includes cooling the composite to body temperature of approximately 37° C.

16. A composite osteoimplant comprising: a plurality of bone-derived particles; and a polymer with which the particles have been combined; wherein the composite has an initial phase and a set phase; wherein the set phase is more resistant to mechanical deformation relative to the initial phase.

17. A composite osteoimplant comprising: a plurality of bone-derived particles; and a polymer with which the particles have been combined; wherein the composite has a first phase and a second phase; wherein the second phase is more resistant to mechanical deformation relative to the first phase.

18. The composite osteoimplant of claim 17, wherein the composite can be converted reversibly between the first and second phase.

19. The composite osteoimplant of claim 17, wherein conversion from the first to second phase is irreversible.

* * * * *

UNITED STATES PATENT AND TRADEMARK OFFICE
CERTIFICATE OF CORRECTION

PATENT NO. : 10,080,661 B2
APPLICATION NO. : 15/149920
DATED : September 25, 2018
INVENTOR(S) : Tunc et al.

Page 1 of 2

It is certified that error appears in the above-identified patent and that said Letters Patent is hereby corrected as shown below:

On the Title Page

In Item (72), under "Inventors", in Column 1, Line 4, delete "Todd Boyce," and insert -- Todd M. Boyce, --, therefor.

On Page 3, in Item (56), under "OTHER PUBLICATIONS", in Column 2, Line 33, delete "InerScience" and insert -- InterScience --, therefor.

On Page 4, in Item (56), under "OTHER PUBLICATIONS", in Column 1, Line 10, delete "Cliical" and insert -- Clinical --, therefor.

On Page 4, in Item (56), under "OTHER PUBLICATIONS", in Column 1, Line 12, delete "bering" and insert -- bearing --, therefor.

On Page 4, in Item (56), under "OTHER PUBLICATIONS", in Column 1, Line 15, delete "Interconeectivity withing" and insert -- Interconnectivity within --, therefor.

In the Specification

In Column 1, Line 8, delete "2013," and insert -- 2013, now Pat. No. 9,333,080, --, therefor.

In Column 1, Line 19, delete "2005," and insert -- 2005, now abandoned, --, therefor.

In Column 4, Line 59, delete "glycodide)," and insert -- glycolide), --, therefor.

In Column 4, Line 60, delete "until is" and insert -- until it --, therefor.

In Column 5, Line 3, delete "glycodide)," and insert -- glycolide), --, therefor.

In Column 6, Line 8, delete "Pharmacopeia-25" and insert -- Pharmacopeial-25 --, therefor.

Signed and Sealed this
Twenty-ninth Day of January, 2019

Andrei Iancu
*Director of the United States Patent and Trademark Office*

CERTIFICATE OF CORRECTION (continued)
U.S. Pat. No. 10,080,661 B2

In Column 7, Line 2, delete "removed" and insert -- remove --, therefor.

In Column 9, Line 25, delete "disectomy," and insert -- discectomy, --, therefor.

In Column 9, Line 26, delete "cerival" and insert -- cervical --, therefor.

In Column 11, Line 1, delete "(e.g., dextran (poly(dextrose))," and insert -- (e.g., dextran (poly(dextrose))), --, therefor.

In Column 13, Line 37, delete "posses" and insert -- possess --, therefor.

In Column 13, Line 40, delete "posses" and insert -- possess --, therefor.

In Column 14, Line 13, delete "defatting/disinfecant" and insert -- defatting/disinfectant --, therefor.

In Column 15, Line 41, delete "in the are" and insert -- in are --, therefor.

In Column 18, Line 3, delete "variety" and insert -- variety of --, therefor.

In Column 18, Line 41, delete "radioopaque," and insert -- radiopaque, --, therefor.

In Column 20, Line 11, delete "to the to the" and insert -- to the --, therefor.

In Column 23, Line 61, delete "Volksmann's canals," and insert -- Volkmann's canals, --, therefor.

In Column 28, Line 37, delete "polyhydroxyvalyrate," and insert -- polyhydroxyvalerate, --, therefor.

In Column 30, Lines 4-5, delete "polytetrafluroethylene" and insert -- polytetrafluoroethylene --, therefor.

In Column 31, Line 24, delete "bibutyl maleate" and insert -- dibutyl maleate --, therefor.

In Column 31, Line 30, delete "trimehtylcitrate" and insert -- trimethylcitrate --, therefor.

In Column 33, Line 13, delete "bout" and insert -- about --, therefor.

In Column 33, Line 66, delete "elonganted," and insert -- elongated, --, therefor.

In Column 39, Line 31, delete "coposite" and insert -- composite --, therefor.